(12) United States Patent
Bates

(10) Patent No.: US 8,187,221 B2
(45) Date of Patent: May 29, 2012

(54) NANOTUBE-REINFORCED BALLOONS FOR DELIVERING THERAPEUTIC AGENTS WITHIN OR BEYOND THE WALL OF BLOOD VESSELS, AND METHODS OF MAKING AND USING SAME

(75) Inventor: Mark C. Bates, Encinitas, CA (US)

(73) Assignee: Nexeon MedSystems, Inc., Charleston, WV (US)

( * ) Notice: Subject to any disclaimer, the term of this patent is extended or adjusted under 35 U.S.C. 154(b) by 61 days.

(21) Appl. No.: 12/172,168

(22) Filed: Jul. 11, 2008

(65) Prior Publication Data
US 2010/0010470 A1 Jan. 14, 2010

(51) Int. Cl.
A61M 31/00 (2006.01)

(52) U.S. Cl. ............... 604/103.01; 604/103.06

(58) Field of Classification Search ............... 604/96.01, 604/97.01–98.02, 103.01, 103.06, 103.08, 604/99.01–103, 103.02–103.05, 103.07, 604/103.09–103.14, 509
See application file for complete search history.

(56) References Cited

U.S. PATENT DOCUMENTS

| | | | |
|---|---|---|---|
| 5,100,429 A | 3/1992 | Sinofsky et al. |
| 5,213,561 A | 5/1993 | Weinstein et al. |
| 5,213,576 A | 5/1993 | Abiuso et al. |
| 5,250,034 A | 10/1993 | Appling et al. |
| 5,254,089 A | 10/1993 | Wang |
| 5,302,369 A | 4/1994 | Day et al. |
| 5,306,250 A | 4/1994 | March et al. |
| 5,318,531 A | 6/1994 | Leone |
| 5,328,469 A | 7/1994 | Coletti |
| 5,328,471 A | 7/1994 | Slepian |
| 5,336,178 A | 8/1994 | Kaplan et al. |
| 5,354,279 A | 10/1994 | Höfling |
| 5,458,568 A | 10/1995 | Racchini et al. |

(Continued)

FOREIGN PATENT DOCUMENTS

EP 0567788 A1 3/1993

(Continued)

OTHER PUBLICATIONS

Bal. S. et al.. "Carbon Nanotube Reinforced Polymer Composites—A State of the Art." Bull. Mater. Sci. (2007) 30(4):379-386.

(Continued)

Primary Examiner — Kevin C Sirmons
Assistant Examiner — Kami A Bosworth
(74) Attorney, Agent, or Firm — Jones Day; Nicola A. Pisano; Christopher C. Bolten

(57) ABSTRACT

A dilatation catheter for delivering a therapeutic agent within a body lumen having a wall with a thickness is provided having a balloon having a flexible wall including a polymer with dispersed nanotubes and pores configured to close below a predefined pressure and to open at or above a predefined pressure. In some embodiments, an actuator is provided to controllably inflate the balloon with a fluid at a pressure sufficient to bring the flexible wall of the balloon into contact with at least a portion of the wall of the body lumen but below the predefined pressure, and to controllably increase the pressure of the fluid within the inflated balloon to at least the predefined pressure at a rate and with a force sufficient to deliver the therapeutic agent from the pores and through at least a portion of the thickness of the wall of the body lumen.

21 Claims, 18 Drawing Sheets

U.S. PATENT DOCUMENTS

| | | | |
|---|---|---|---|
| 5,601,802 | A | 2/1997 | Hemmi et al. |
| 5,611,775 | A | 3/1997 | Machold et al. |
| 5,688,486 | A | 11/1997 | Watson et al. |
| 5,792,106 | A | 8/1998 | Mische |
| 5,800,392 | A | 9/1998 | Racchini |
| 5,871,468 | A | 2/1999 | Kramer et al. |
| 6,039,757 | A | 3/2000 | Edwards et al. |
| 6,048,332 | A | 4/2000 | Duffy et al. |
| 6,129,901 | A | 10/2000 | Moskovits et al. |
| 6,265,466 | B1 | 7/2001 | Glatkowski et al. |
| 6,355,225 | B1 | 3/2002 | Alford et al. |
| 6,485,500 | B1 * | 11/2002 | Kokish et al. ............ 606/194 |
| 6,585,926 | B1 | 7/2003 | Mirzaee |
| 6,592,545 | B1 | 7/2003 | Bellhouse et al. |
| 6,623,452 | B2 | 9/2003 | Chien et al. |
| 6,635,027 | B1 | 10/2003 | Cragg et al. |
| 6,685,669 | B2 | 2/2004 | Bellhouse et al. |
| 6,758,828 | B2 | 7/2004 | Hammer et al. |
| 6,765,144 | B1 | 7/2004 | Wang et al. |
| 6,786,889 | B1 | 9/2004 | Musbach et al. |
| 6,936,653 | B2 | 8/2005 | McElrath et al. |
| 7,029,751 | B2 | 4/2006 | Fan et al. |
| 7,037,562 | B2 | 5/2006 | Jimenez |
| 7,115,299 | B2 | 10/2006 | Kokish |
| 7,133,725 | B2 | 11/2006 | Stirbl et al. |
| 7,202,667 | B2 | 4/2007 | Barbic |
| 7,226,531 | B2 | 6/2007 | Lo et al. |
| 7,311,655 | B2 | 12/2007 | Schaart |
| 7,338,657 | B2 | 3/2008 | Vogel et al. |
| 7,635,510 | B2 | 12/2009 | Horn et al. |
| 7,758,892 | B1 | 7/2010 | Chen et al. |
| 2002/0156469 | A1 | 10/2002 | Yon et al. |
| 2003/0065355 | A1 | 4/2003 | Weber |
| 2003/0093107 | A1 | 5/2003 | Parsonage et al. |
| 2003/0143350 | A1 | 7/2003 | Jimenez |
| 2003/0220518 | A1 | 11/2003 | Bolskar et al. |
| 2004/0101644 | A1 | 5/2004 | Kinoshita et al. |
| 2004/0106987 | A1 | 6/2004 | Palasis et al. |
| 2004/0111141 | A1 | 6/2004 | Brabec et al. |
| 2004/0138733 | A1 | 7/2004 | Weber et al. |
| 2004/0166152 | A1 | 8/2004 | Hirsch et al. |
| 2004/0197638 | A1 | 10/2004 | McElrath et al. |
| 2004/0236308 | A1 | 11/2004 | Herweck et al. |
| 2005/0027248 | A1 | 2/2005 | Suzuki et al. |
| 2005/0038498 | A1 | 2/2005 | Dubrow et al. |
| 2005/0096509 | A1 | 5/2005 | Olson |
| 2005/0124976 | A1 | 6/2005 | Devens et al. |
| 2005/0165301 | A1 | 7/2005 | Smith et al. |
| 2005/0171425 | A1 | 8/2005 | Burke |
| 2005/0186243 | A1 | 8/2005 | Hunter et al. |
| 2005/0249656 | A1 | 11/2005 | Smalley et al. |
| 2005/0261670 | A1 | 11/2005 | Weber |
| 2005/0261721 | A1 | 11/2005 | Radisch et al. |
| 2006/0008606 | A1 | 1/2006 | Horn et al. |
| 2006/0032508 | A1 | 2/2006 | Simpson |
| 2006/0051535 | A1 | 3/2006 | Arney et al. |
| 2006/0079836 | A1 | 4/2006 | Holman et al. |
| 2006/0100696 | A1 | 5/2006 | Atanasoska et al. |
| 2006/0184112 | A1 | 8/2006 | Horn et al. |
| 2006/0204738 | A1 | 9/2006 | Dubrow et al. |
| 2006/0251726 | A1 | 11/2006 | Lin et al. |
| 2007/0025918 | A1 | 2/2007 | Hurd |
| 2007/0077432 | A1 | 4/2007 | Nagasaki et al. |
| 2007/0100279 | A1 | 5/2007 | Bates |
| 2007/0110658 | A1 | 5/2007 | Liang et al. |
| 2007/0135803 | A1 | 6/2007 | Belson |
| 2007/0191766 | A1 | 8/2007 | McMorrow |
| 2007/0198090 | A1 | 8/2007 | Abdou |
| 2007/0282247 | A1 | 12/2007 | Desai et al. |
| 2008/0003182 | A1 | 1/2008 | Wilson et al. |
| 2008/0039854 | A1 | 2/2008 | Rabiner |
| 2008/0045865 | A1 | 2/2008 | Kislev |
| 2008/0071353 | A1 | 3/2008 | Weber et al. |
| 2010/0158193 | A1 | 6/2010 | Bates |

FOREIGN PATENT DOCUMENTS

| | | | |
|---|---|---|---|
| EP | | 1388346 A1 | 2/2004 |
| EP | | 1829567 A1 | 9/2007 |
| WO | WO 2004/060472 A1 | | 7/2004 |
| WO | WO 2005/112845 A1 | | 1/2005 |
| WO | WO 2005/056097 A1 | | 6/2005 |
| WO | WO 2005/115496 A1 | | 12/2005 |
| WO | WO 2006/052538 A2 | | 5/2006 |
| WO | WO 2007/149776 A2 | | 12/2007 |

OTHER PUBLICATIONS

U.S. Appl. No. 12/342,013, filed Dec. 22, 2008, Bates.

U.S. Appl. No. 13/051,351, filed Mar. 18, 2011, D'Aquanni et al.

* cited by examiner

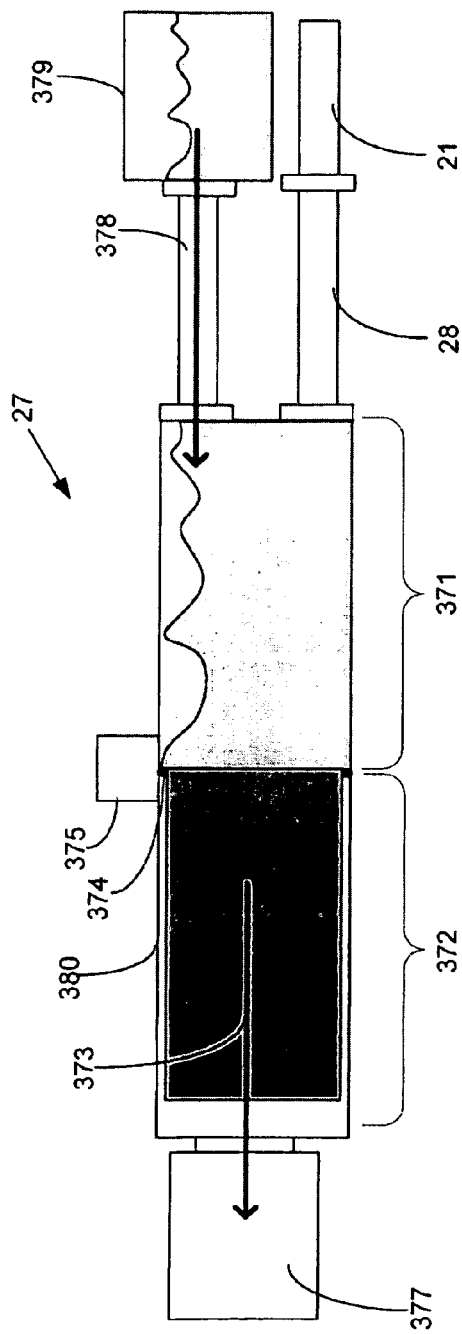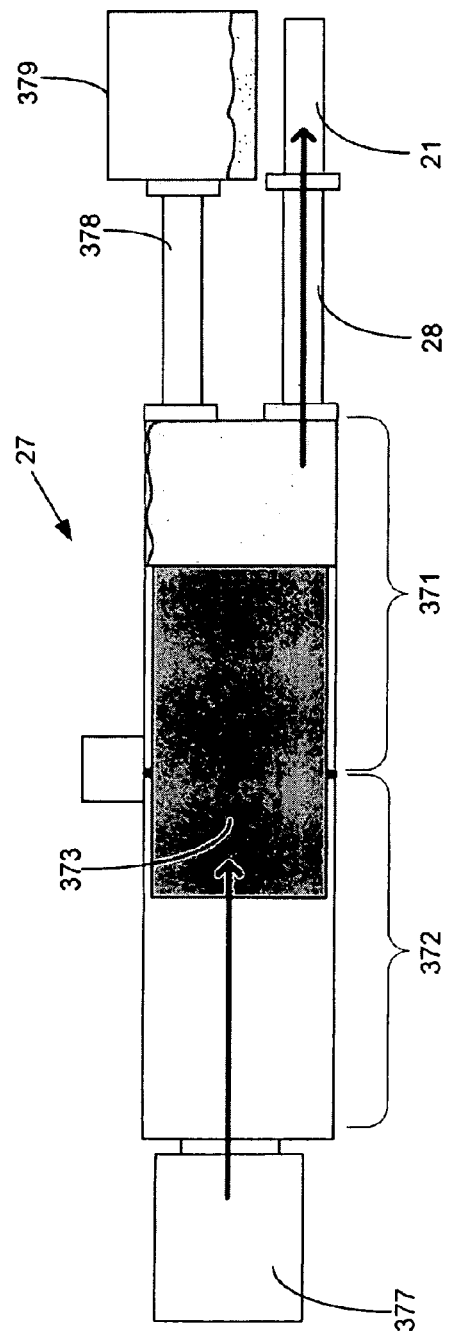
FIG. 3D
FIG. 3E

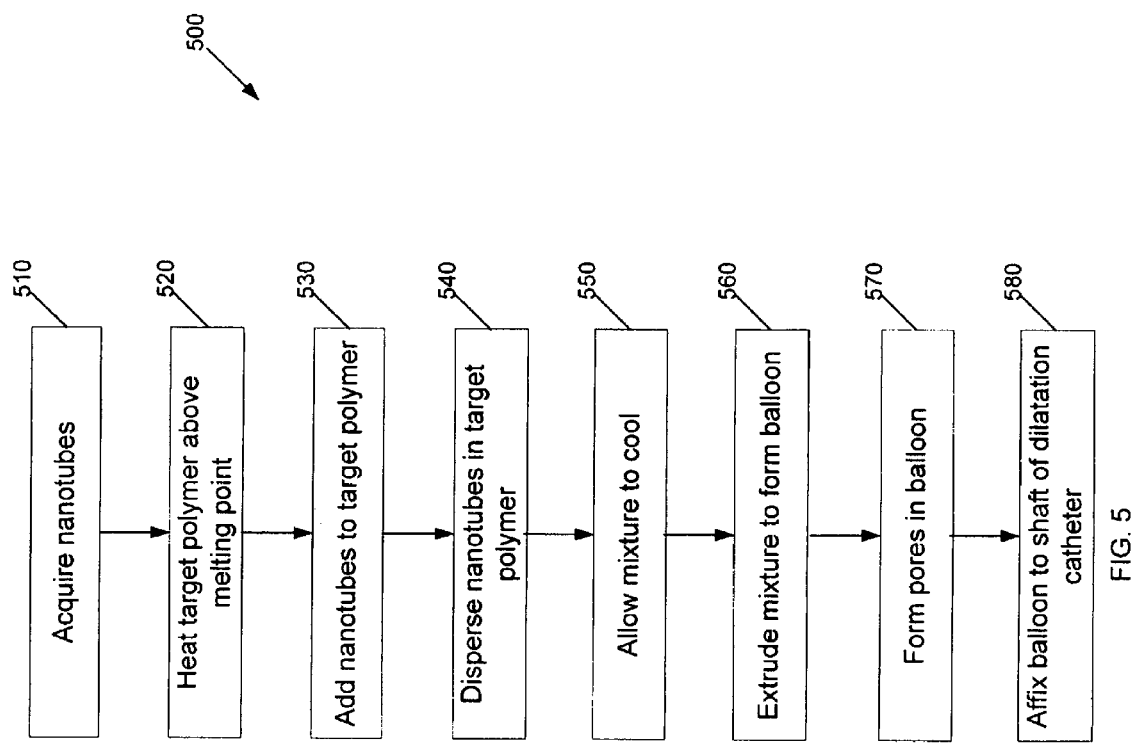

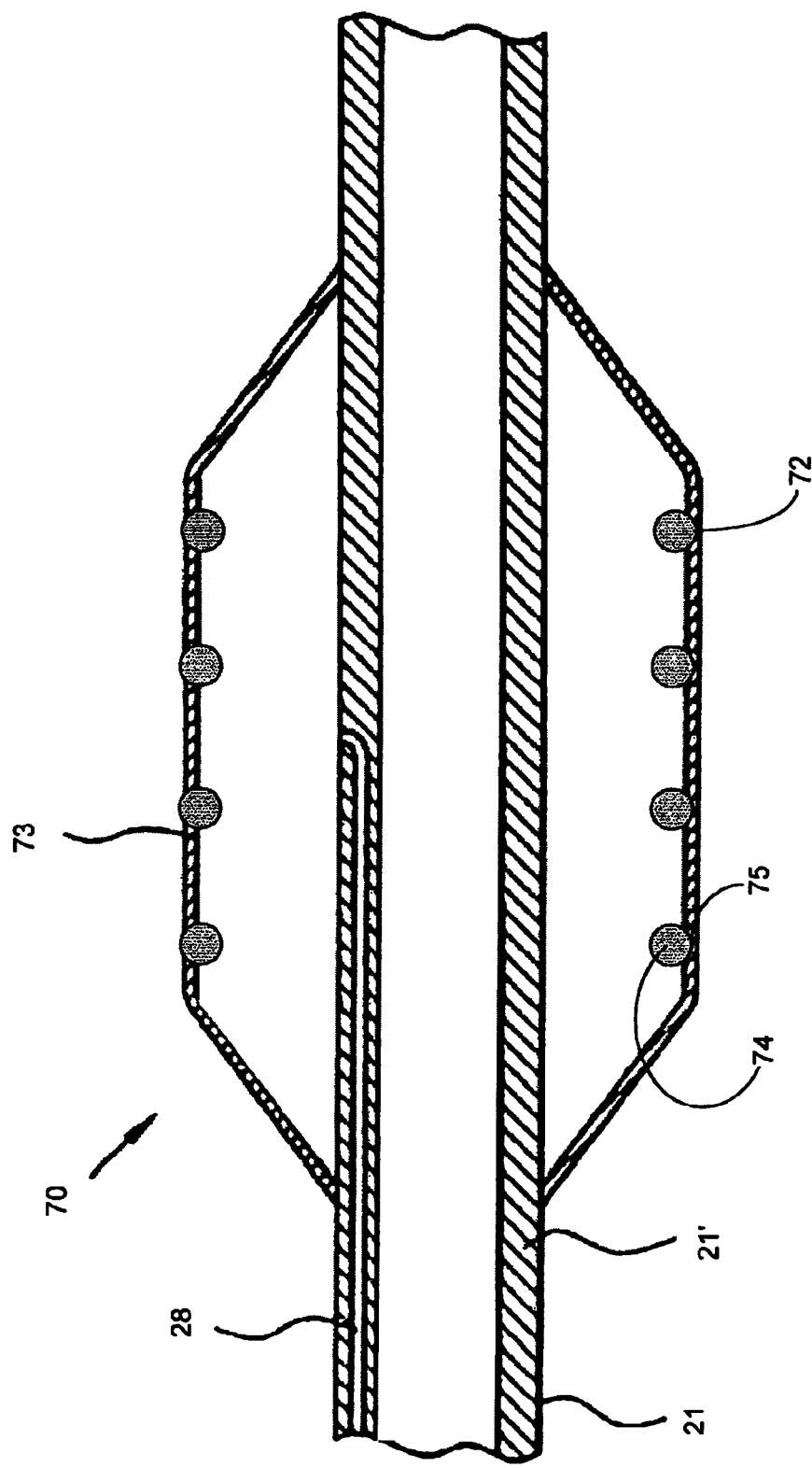

NANOTUBE-REINFORCED BALLOONS FOR DELIVERING THERAPEUTIC AGENTS WITHIN OR BEYOND THE WALL OF BLOOD VESSELS, AND METHODS OF MAKING AND USING SAME

FIELD

This application generally relates to balloons for delivering therapeutic agents within blood vessels.

BACKGROUND

Percutaneous transluminal coronary angioplasty (PTCA) is a less invasive surgical alternative for patients with vessel narrowing due to atherosclerosis and other diseases and conditions. In a conventional PTCA procedure, a dilatation catheter is inserted into the cardiovascular system, under local anesthesia, to a desired position within the culprit vessel. The catheter includes an inflatable balloon formed of a non-porous membrane at its distal end, and means for inflating the balloon. As is illustrated in FIG. 1A, balloon 10 is positioned so that it traverses or crosses stenotic lesion 12 within artery 14. As is illustrated in FIG. 1B, balloon 10 then is inflated with a radiopaque liquid at relatively low pressures. This liquid compresses balloon 10 against lesion 12, and expands artery 14 in a direction generally perpendicular to its wall, thereby dilating the lumen of the artery. Such compression may cause damage within the arterial wall, illustrated by the wavy lines in FIG. 1B. Following this procedure, balloon 10 is deflated and the catheter withdrawn.

Despite the general success of PTCA, the dilated lesion can undergo an aggressive neointimal healing response resulting in restenosis within the first year after dilation, as is illustrated in FIG. 1C. Such restenosis may be amplified by abrupt recoil of artery 14 resulting from lesion elasticity, vessel dissection, vasospasms, or the like, e.g., resulting from damage to the intima or media of the arterial wall. Alternately, or additionally, restenosis of the artery may occur. For example, an inflammatory response to PTCA, e.g., due to damage to the artery, may induce tissue proliferation 12' around the site of the stenotic lesion. Thrombotic occlusions may also block the artery near the site of the stenotic lesion. As FIG. 1C illustrates, restenosis of the artery may arise from a thickening of the arterial wall and/or a narrowing of the lumen of the artery, and the subject may need additional treatment in order to restore patency.

Stenting is a commonplace technique used to try to prevent and/or treat restenosis, and frequently is employed as an adjunct to PTCA. During the stenting procedure, a metal mesh (stent) is deployed against the wall of the dilated artery and serves as a scaffold to hold open the artery. However, stents may occlude due to thrombosis, or the formation of a clot in the stent. Because the stent is a foreign object, the body's immune system also may respond with cell proliferation, resulting in restenosis. Such proliferation may be reduced by coating the stent with drugs such as paclitaxel, to reduce the growth of neointimal scar tissue, but such drugs also limit healing of the arterial wall and thus increase the chance of delayed clot formation.

It has been suggested that restenosis may be reduced by applying a drug directly to the lesion during the PTCA procedure. For example, U.S. Pat. No. 5,306,250 to March et al. discloses a porous membrane that is mechanically or hydraulically expanded into contact with a stenotic lesion. After the membrane is expanded, a liquid containing a drug such as heparin or colchicines is caused to flow through the pores in the membrane and into contact with the lesion. The expansion and drug-delivery mechanisms are independent of each other in order to avoid leakage of the drug through the pores until the membrane is fully expanded.

U.S. Pat. No. 5,458,568 to Racchini et al. discloses a selectively permeable balloon that both dilates a passageway and delivers a drug, such as a fixative. The permeability of the balloon is controlled by wetting the pores of the membrane using a pressure based on the surface tension of the liquid, the contact angle of the liquid on the membrane, and the pore diameter, and/or applying a current, and/or applying high frequency sound waves. The fixative quickly kills or otherwise renders the tissue inert, and hardens the vascular structure in a dilated condition. Racchini et al. discloses that such fixation prevents or reduces re-closure due to vasospasm, and also retards or stops the biological processes that lead to restenosis.

U.S. Pat. No. 5,354,279 to Hofling discloses a catheter that includes hollow needles that can be used to inject medicine within the wall of a blood vessel.

Although the delivery of a drug such as heparin to a stenotic lesion may be useful, blood flowing through the artery may quickly wash the drug away from the affected area, thus reducing the efficacy of the treatment. Such drugs also have little effect on vessel recoil and vasospasm. While Hofling discloses needles for injecting a drug directly into the wall of a blood vessel, the number of needles that can be used is limited, thus constraining the extent to which the medicine can be delivered. Additionally, the gauge of the needles used is relatively large, which increases the risk of dissection. While fixation of an artery such as disclosed in Racchini et al. may reduce the chances both of restenosis and recoil, the mechanism by which this fixation is accomplished—killing and hardening arterial tissue—impairs the artery's ability to heal itself and may potentially damage the surrounding healthy tissue.

In view of the foregoing, it would be useful to provide a balloon that dilates a blood vessel and that may be used to deliver a therapeutic agent to the dilate blood vessel without rupturing either the balloon or the blood vessel.

It would also be useful to provide a balloon that delivers a therapeutic agent at a sufficient pressure and velocity to penetrate to a controlled depth within, or even beyond, the wall of a dilated blood vessel, without rupturing either the balloon or the blood vessel.

It would also be useful to provide a therapeutic agent that, when delivered to a controlled depth within, or even beyond, the wall of a dilated blood vessel, inhibits recoil and restenosis of the blood vessel without killing a portion of the blood vessel.

SUMMARY

In view of the foregoing, it is an object of the invention to provide a balloon that dilates a blood vessel and that may be used to deliver a therapeutic agent to the dilated blood vessel without rupturing either the balloon or the blood vessel.

It is also an object of the invention to provide a balloon that delivers a therapeutic agent at a sufficient pressure and velocity to penetrate to a controlled depth within, or even beyond, the wall of a dilated blood vessel, without rupturing either the balloon or the blood vessel.

It is also an object of the invention to provide a therapeutic agent that, when delivered to a controlled depth within, or even beyond, the wall of a dilated blood vessel, inhibits recoil and restenosis of the blood vessel without killing a portion of the blood vessel.

These and other objects of the invention are accomplished by providing a dilatation catheter for delivering a therapeutic agent within a body lumen, the body lumen having a wall with a thickness. The dilatation catheter includes an elongated shaft having proximal and distal ends and a lumen therebetween; and a balloon affixed to the elongated shaft near the distal end. The balloon has a flexible wall that includes a polymer with a plurality of nanotubes or other strengthening fabric dispersed therein. The flexible wall has a plurality of pores defined therein, the pores being configured to close below a predefined pressure and to open at or above a predefined pressure.

Some embodiments further include a pressurized reservoir of fluid in fluidic communication with the balloon via the lumen in the shaft; and an actuator for controllably inflating the balloon with the fluid at a pressure sufficient to bring the flexible wall of the balloon into contact with at least a portion of the wall of the body lumen but below the predefined pressure, and for controllably increasing the pressure of the fluid within the inflated balloon to at least the predefined pressure at a rate and with a force sufficient to deliver the therapeutic agent from the pores and through at least a portion of the thickness of the wall of the body lumen. In some embodiments, the actuator controllably increases the pressure of the liquid within the inflated balloon to a selected pressure at a rate and with a force sufficient to deliver the therapeutic agent from the pores and through the entirety of at least one of a tunica intima, a tunica media, and a tunica adventitia of the body lumen. In some embodiments, the therapeutic agent is particulate and is disposed within the pores, so that actuation of the actuator controllably increases the pressure of the liquid within the inflated balloon to at least the predefined pressure at a rate and with a force sufficient to eject the therapeutic agent from the pores and through at least a portion of the thickness of the wall of the body lumen.

In some embodiments, the nanotubes or other fabric form a reinforcing web within the flexible wall of the balloon. In some embodiments, the nanotubes are substantially evenly dispersed in the polymer. In some embodiments, the nanotubes are present in a concentration of less than 5% w/w in the polymer. In some embodiments, the predefined pressure is based at least in part on a size of the pores, a thickness of the flexible wall, a composition of the polymer, and a concentration of nanotubes or fabric in the polymer.

In some embodiments, the liquid includes the therapeutic agent and a pharmaceutically acceptable carrier, so that actuation of the actuator controllably increases the pressure of the liquid within the inflated balloon to at least the predefined pressure at a rate and with a force sufficient to jet the liquid through the pores and through at least a portion of the thickness of the wall of the body lumen. In some embodiments, the therapeutic agent includes an agent for creating an in-situ stent within the wall of the body lumen. In some embodiments, the agent includes at least one of an enzyme, a cross-linking agent, a small molecule, a protein, and an antibody selected to modify an elasticity of an intracellular matrix. In some embodiments, the therapeutic agent is selected from the group consisting of: antithrombotics, thrombolytic agents, antiproliferative agents, anti-inflammatory agents, growth factors, smooth muscle cell migration and matrix degradation inhibitors, and re-endothelialization agents.

In accordance with another aspect of the invention, a method of delivering a therapeutic agent within a body lumen having a wall with a thickness is provided. The inventive method includes: inserting into the body lumen at least a portion of a dilatation catheter, the dilatation catheter including: an elongated shaft having proximal and distal ends and a lumen therebetween; and a balloon affixed to the elongated shaft near the distal end. The balloon has a flexible wall that includes a polymer with a plurality of nanotubes or fabric dispersed therein. The flexible wall also has a plurality of pores defined therein that are configured to close below a predefined pressure and to open at or above a predefined pressure. The method includes controllably inflating the balloon with the fluid at a pressure sufficient to bring the flexible wall of the balloon into contact with at least a portion of the wall of the body lumen but below the predefined pressure; and controllably increasing the pressure of the liquid within the inflated balloon to at least the predefined pressure at a rate and with a force sufficient to deliver the therapeutic agent from the pores and through at least a portion of the thickness of the wall of the body lumen.

BRIEF DESCRIPTION OF THE DRAWINGS

The above and other objects of the invention will be apparent upon consideration of the following detailed description, taken in conjunction with the accompanying drawings, in which like reference characters refer to like parts throughout, and in which:

FIGS. 3D-3E illustrate a pressure-controllable fluid source that may be used to inflate a nanotube-reinforced balloon and to deliver a therapeutic agent from pores in the inflated nanotube-reinforced balloon, according to some embodiments of the present invention.

FIG. 5 illustrates a method of forming the nanotube-reinforced balloon of FIGS. 2A-2C, according to some embodiments of the present invention.

FIG. 7A illustrates a longitudinal sectional view of a nanotube-reinforced balloon capable of delivering a solid therapeutic agent within a blood vessel wall that may be used in the dilatation catheter illustrated in FIG. 2A, according to some embodiments of the present invention.

DETAILED DESCRIPTION OF THE PREFERRED EMBODIMENTS

Figure 1C:
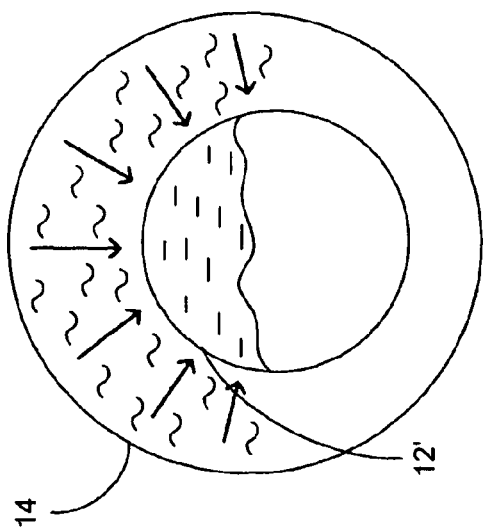
FIG. 1C illustrates a cross-sectional view of an artery undergoing restenosis following treatment with a conventional balloon.
Figure 1B:
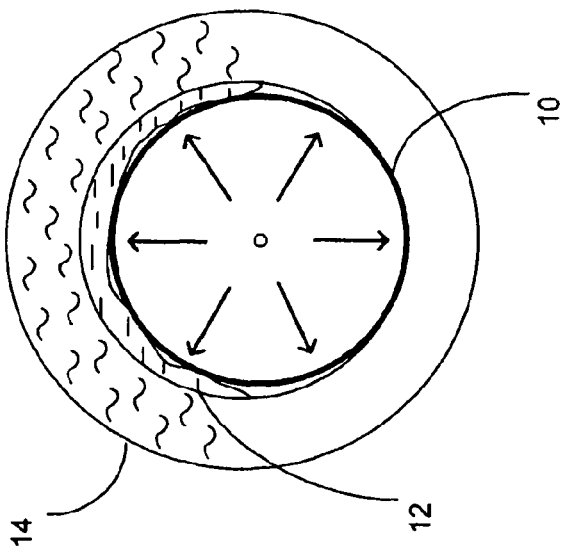
FIG. 1B illustrates a cross-sectional view of an inflated, conventional balloon compressing a stenotic lesion in an artery.
Figure 1A:
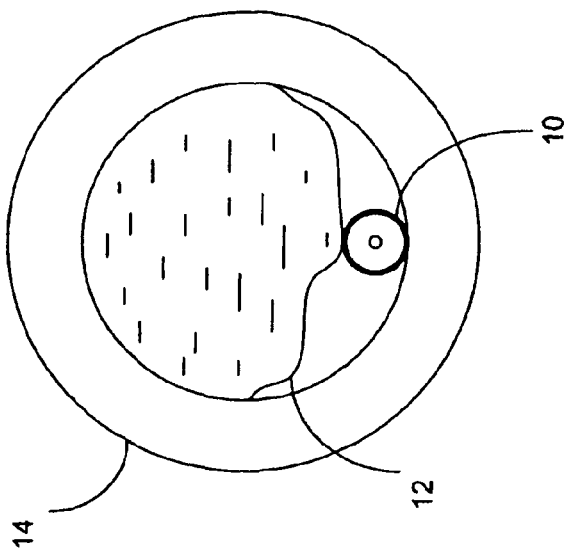
FIG. 1A illustrates a cross-sectional view of a deflated, conventional balloon positioned adjacent a stenotic lesion in an artery.

Embodiments of the invention provide nanotube-reinforced balloons for delivering therapeutic agents within or beyond the wall of blood vessels, methods of making same, and methods of using same.

Specifically, embodiments of the invention provide balloons having flexible wall made of a polymer-nanotube matrix with a plurality of therapeutic agent-dispensing pores defined therein. The nanotube-reinforced balloons are inflated to expand a blood vessel, e.g., an artery that is at least partially closed by a stenotic lesion, and then subjected to a pressure impulse exceeding a predefined threshold. This pressure impulse causes the balloon to rapidly eject therapeutic agent from the pores and through at least a portion of the thickness of the wall of the blood vessel, or optionally through the entire thickness of the wall of the blood vessel. The therapeutic agent thus becomes embedded within the wall of the blood vessel, or disposed outside of the wall of the blood vessel, and thus performs its intended function without substantial risk of being washed away by blood flowing through the blood vessel.

The pores in the nanotube-reinforced balloons are configured to be closed when fluid within the balloon is below a predefined threshold pressure. This inhibits the therapeutic agent from leaking out of the pores while the balloon is positioned within the blood vessel and while the balloon is inflated with the fluid to dilate the blood vessel. The pores in the nanotube-reinforced balloons are configured to open only when the fluid within the balloon reaches or exceeds the predefined threshold pressure. Once the fluid reaches that threshold pressure, the pores rapidly open and emit or eject the therapeutic agent at a pressure and velocity sufficient to penetrate the wall of the blood vessel to a desired thickness. After emitting or ejecting the therapeutic agent, once the pressure drops again below the threshold pressure, the pores close. Thus, the pores in the nanotube-reinforced balloons are valves that open only at a predefined pressure and otherwise remain closed. Whereas U.S. Pat. No. 5,354,279 discloses mechanical needles which are therefore limited in number and of relatively large size, nanotube-reinforced balloon 30 can be thought of as having a large number of tiny "virtual needles" capable of delivering therapeutic agent within the wall of a blood vessel.

The flexible wall in which the pores are defined are formed of a polymer with a plurality of carbon nanotubes substantially evenly dispersed therein. The carbon nanotubes, thus dispersed, provide resistance to tear propagation and thus enable the pores to withstand rapid pressure changes without rupturing. Carbon nanotubes have an exceptionally high tensile strength and elastic modulus, and may be used to form a strong, interconnected, reinforcing web within the wall of a balloon that prevents tears from propagating from the pores. Selection of the appropriate concentration of nanotubes, polymer composition, and wall thickness allows pores of any desired size to be formed in the wall to be sufficiently pressurized to deliver therapeutic agent to a desired depth in a blood vessel wall, without rupturing.

In some embodiments, the pores emit jets of a pressurized fluid that includes a therapeutic agent and a pharmaceutically acceptable carrier. Such pores are defined within the flexible wall of the balloon and extend from the interior to the exterior of the balloon. The balloon is inflated by filling the interior of the balloon with a fluid at a pressure lower than the predefined threshold pressure, such that the pores remain closed. The pressure of the fluid within the interior of the balloon then is rapidly increased to a pressure at least as high as the predefined threshold pressure, which causes the pores to open. Fluid then jets from the interior portion of the balloon into the wall of the blood vessel, thus delivering the therapeutic agent to a defined thickness within, or even beyond, the wall of the blood vessel. In some embodiments, the therapeutic agent is lipophilic.

In other embodiments, the pores eject a solid, particulate therapeutic agent, which may be mixed with a solid, particulate, pharmaceutically acceptable carrier. Similarly to the pores that transmit fluid, such pores are disposed within the flexible wall of the balloon and extend through the thickness of the wall of the balloon. A plurality of sacs, one for each pore, are affixed to the flexible wall inside the balloon. Each sac has an interior portion that holds the solid, particulate therapeutic agent, and that is kept shut by the pore until actuation of the balloon. The balloon is inflated by filling the interior of the balloon with a fluid at a pressure lower than the predefined threshold pressure. The pores remain closed at this pressure. The pressure of the fluid within the interior of the balloon then is rapidly increased to a pressure at least as high as the predefined threshold pressure. This opens the pores, which eject the solid, particulate therapeutic agent from the interior portion of the sacs into the wall of the blood vessel, thus delivering the therapeutic agent to a defined thickness within, or even beyond, the wall of the blood vessel.

The nanotube-reinforced balloons of the present invention enable blood vessels to be therapeutically treated using methods not heretofore available. For example, a nanotube-reinforced balloon may be used to create an in-situ stent within the wall of a blood vessel. By "in-situ stent" it is meant that the mechanical properties of the wall of the blood vessel are modified (e.g., the blood vessel's elasticity reduced) to inhibit restenosis and recoil of the blood vessel. Creating an in-situ stent may inhibit recoil by creating regions within the blood vessel wall that have sufficient strength to hold the blood vessel open, even if vasospasms occur. Another particularly useful aspect of the in-situ stent is that the blood vessel itself remains alive. The mechanical properties of the wall of the blood vessel may be modified, for example, by delivering one or more selected therapeutic agents at a specified depth within the wall (e.g., within the media of the blood vessel) using a nanotube-reinforced balloon, thus modifying the mechanical properties of the wall, for example, by decreasing the elasticity of the wall (increasing hardness). In some embodiments, the therapeutic agent changes the intercellular matrix at a preselected depth, but does not damage or otherwise affect the cells themselves.

Suitable therapeutic agents for creating in-situ stents may include, for example, a selected enzyme, a selected cross-linking agent, a selected small molecule, a selected protein, or a selected antibody. One example of a suitable therapeutic agent is a polymer that cross-links in the presence of an intercellular matrix. Another example of a suitable therapeutic agent is an enzyme or crosslinking agent that changes the intracellular matrix elasticity. Another example of a suitable therapeutic agent is an antibody-activated complex that is activated by molecules in an intercellular matrix. In addition to the therapeutic agent that causes formation of the in-situ stent, other therapeutic agents also may be deposited in the wall of the blood vessel, e.g., agents that inhibit restenosis.

Figure 2A:
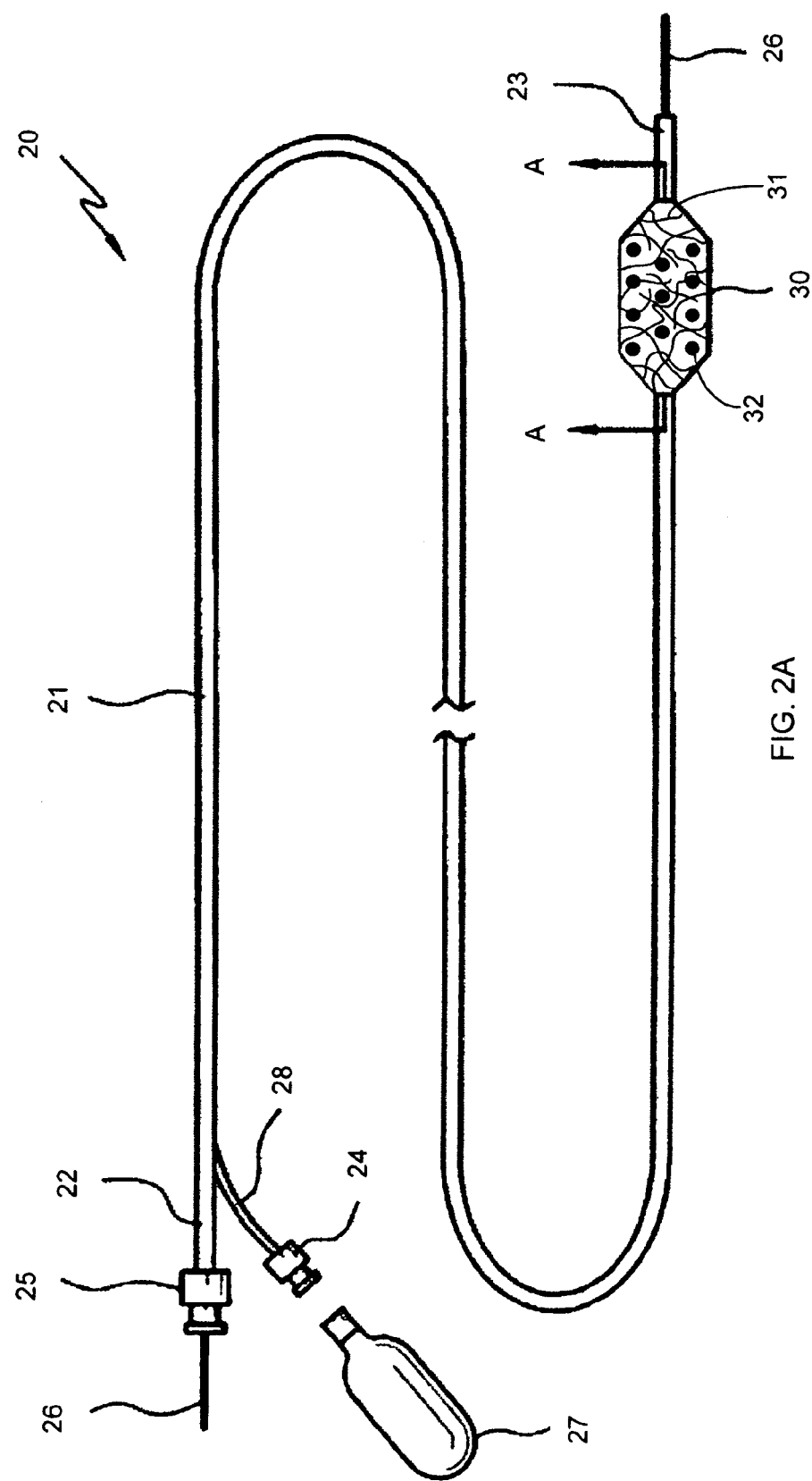
FIG. 2A illustrates a high-level plan view of a dilatation catheter that includes a nanotube-reinforced balloon capable of delivering a fluidic therapeutic agent within blood vessel wall, according to some embodiments of the present invention.

FIG. 2A illustrates a high-level plan view of a dilatation catheter constructed in accordance with some embodiments of the present invention. Dilatation catheter 20 includes shaft 21, proximal end 22, distal end 23, inflation port 24, manifold 25, guide wire 26, fluid source 27, inflation lumen 28, and nanotube-reinforced balloon 30.

Fluid source 27 is in fluidic communication with balloon 30 through inflation lumen 28. Fluid source 27, e.g., pressurized gas such as carbon dioxide ($CO_2$), air, or other gas or fluid, may be attached directly to inflation port 24, or may alternatively pass first through a regulation device to control pressure, flow rate, and/or other fluid properties. As described in greater detail below, the pressure of fluid source 27 may be varied over time to inflate nanotube-reinforced balloon 30 and to deliver therapeutic agents into the wall of a blood vessel once balloon 30 is inflated. In some embodiments, fluid source 27 is a pressurized liquid that includes both a contrast agent allowing the dilatation catheter to be imaged in situ using radiography, and a therapeutic agent to be delivered into the wall of a blood vessel.

Figure 2B:
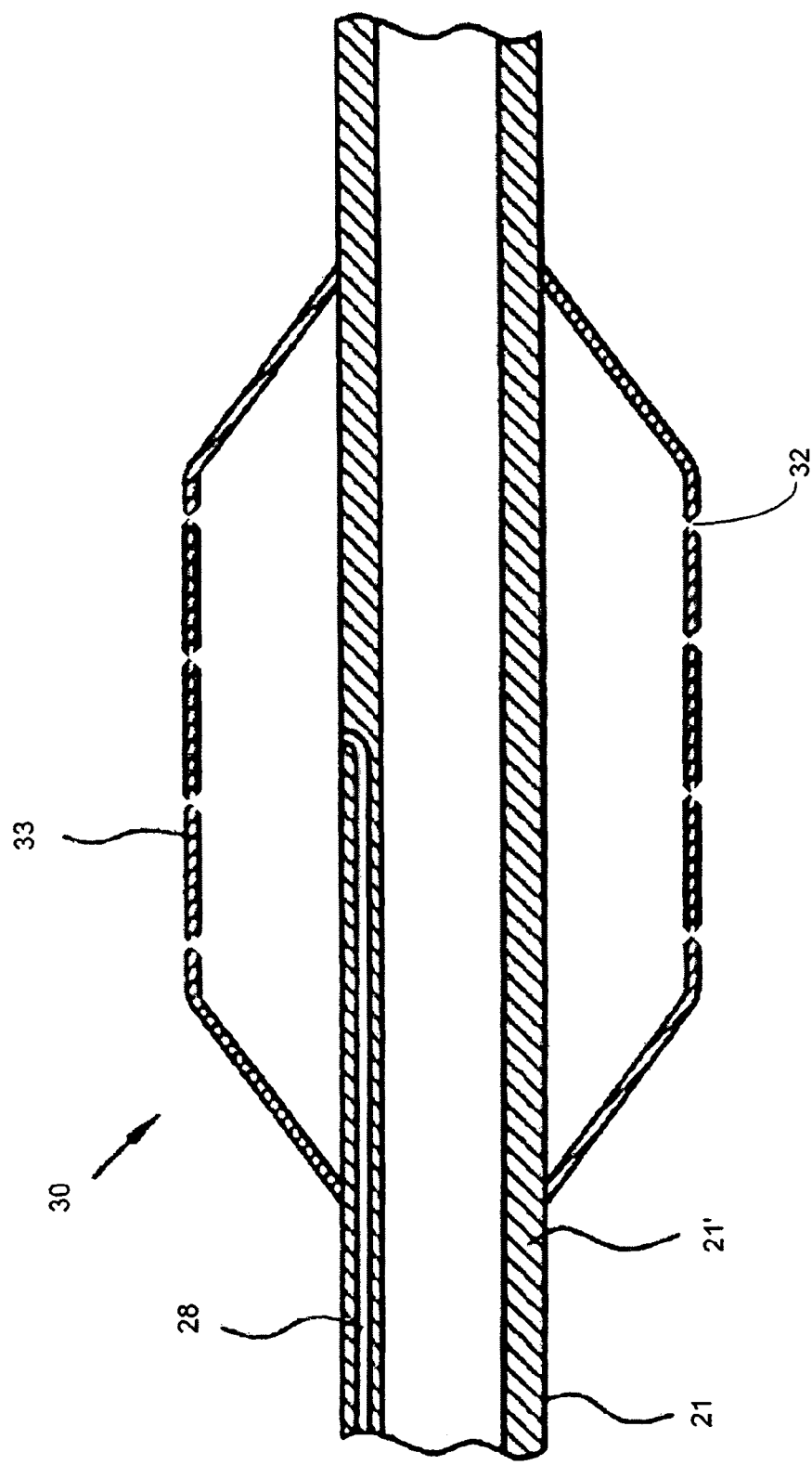
FIG. 2B illustrates a longitudinal sectional view of the nanotube-reinforced balloon of FIG. 2A.

As illustrated in greater detail in FIG. 2B, nanotube-reinforced balloon 30 includes flexible wall 33 affixed to shaft 21. Inflation lumen 28 passes through wall 21' of shaft 21, so that a distal end of inflation lumen 28 communicates with the space defined between the outer surface of shaft 21 and the inner surface of the flexible wall 33. The proximal end of inflation lumen 28 is coupled to inflation port 24. Inflation port 24 is coupled to fluid source 27 (not shown in FIG. 2B) that contains a therapeutic agent, and optionally also a contrast agent.

Figure 2C:
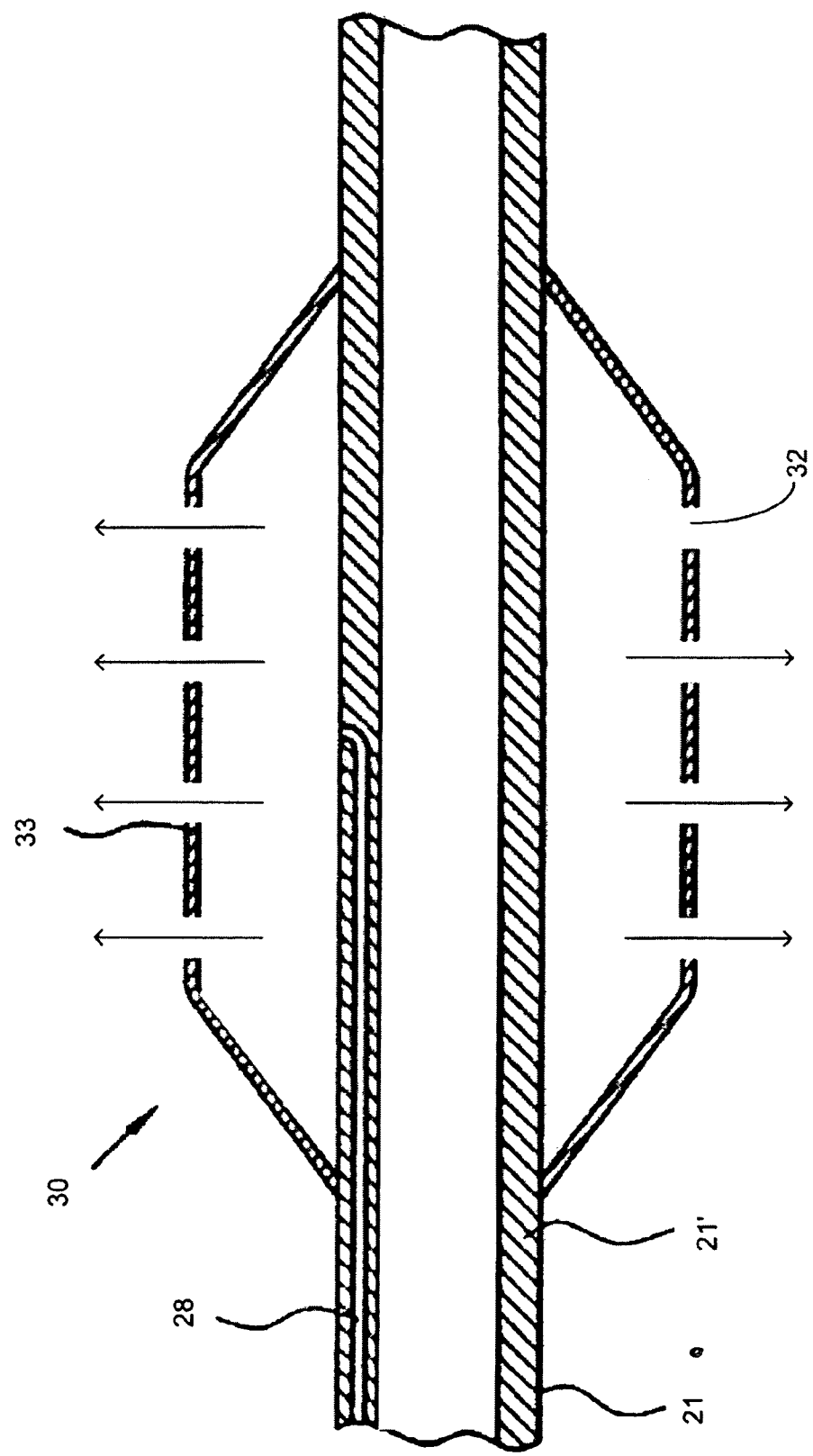
FIG. 2C illustrates a longitudinal sectional view of the nanotube-reinforced balloon of FIG. 2A.

Flexible wall 33 of nanotube-reinforced balloon 30 is formed from a composition that includes a plurality of carbon nanotubes 31 that are substantially evenly dispersed in a polymeric matrix. Pores 32 are defined in flexible wall 33 of balloon 30 and extend through the thickness of wall 33. The pores are configured so as to remain closed until a pressure within the balloon meets or exceeds a predefined threshold pressure. This feature allows the balloon to be inflated to a first, lower pressure (e.g., less than 10 atm, less than 8 atm, or less than 4 atm, or less than 2 atm) to dilate the blood vessel and/or disrupt a stenotic lesion, without the pores opening. As illustrated in FIG. 2C, when the pressure of the fluid within balloon 30 exceeds the predefined threshold pressure (e.g., greater than 10 atm, or greater than 15 atm, or greater than 20 atm, or greater than 25 atm, or greater than 30 atm, or greater than 35 atm), pores 32 open and jet fluid from the interior of balloon 30 to the exterior of balloon 30.

As pressure is applied to nanotube-reinforced balloon 30, flexible wall 33 slightly deforms. The size and shape of pores 32 are selected such that the regions of flexible wall 33 in which the pores 32 are defined sufficiently deform to open pores 32 only at or above a predefined pressure. In addition to the size and shape of pores 32, other factors that affect the pressure at which pores 32 open include the thickness of flexible wall 33, the composition of the polymer, the concentration and type of nanotubes, the number, distribution, and density of pores in wall 33, and the viscosity of the pressurized fluid. For example, different types of therapeutic agents, pharmaceutically acceptable carriers and/or contrast agents may in some circumstances change the resistance of the pores to opening, so the particular composition of the fluid may be preselected to be compatible with the depth to which the therapeutic agent is desired to be delivered within the blood vessel wall.

Without wishing to be bound by theory, it is believed that the resistance of pores in the balloon to opening ($R_{pore}$) is based, in part, on the viscosity of the fluid carrying the therapeutic agent ($V_{Rx}$), the size of the pores ($D_{pore}$), the density of the pores ($\rho_{pore}$) as follows:

$$R_{pore} = V_{Rx}/(\rho_{pore} D_{pore})$$

In many embodiments, the size of the pores $D_{pore}$ varies with pressure; that is, $D_{pore}$ is a function of pressure P, $D_{pore}(P)$. Thus, as $D_{pore}$ changes with pressure (e.g., increases with increasing pressure), the resistance of the pores in the balloon to opening falls. For a given number, distribution, and density of pores in wall 33 and viscosity of the pressurized fluid, the thickness of flexible wall 33, the composition of the polymer, the concentration and type of nanotubes, and the initial size of the pores $D_{pore}(P=0)$ are selected such that below a threshold pressure PT, the pores remain below a threshold size and therefore do not transmit fluid carrying the therapeutic agent, and such that above the threshold pressure PT, the pores exceed the threshold size and thus deliver the therapeutic agent to a defined distance within the blood vessel wall.

In some embodiments, the pores before opening are between 1 nm and 3,000 nm in diameter, e.g., between 1 nm and 100 nm, between 10 nm and 50 nm, between 50 nm and 250 nm, or between 250 nm and 1,000 nm. In some embodiments, the pores after opening are between 5 nm and 10,000 nm in diameter, e.g., between 5 nm and 100 nm, between 10 nm and 50 nm, between 50 nm and 250 nm, between 250 and 1,000 nm, between 1,000 nm and 3,000 nm, or between 1,000 and 5,000 nm. In some embodiments, the pores have a density between 10 to 500,000,000 per square centimeter, e.g., between 10 and 200 per square centimeter, between 200 and 5000 per square centimeter, between 5000 and 100,000 per square centimeter, or between 100,000 and 500,000,000 per square centimeter. In some embodiments, the thickness of flexible wall 33 is between 0.05-0.1 mm.

Figure 2D:
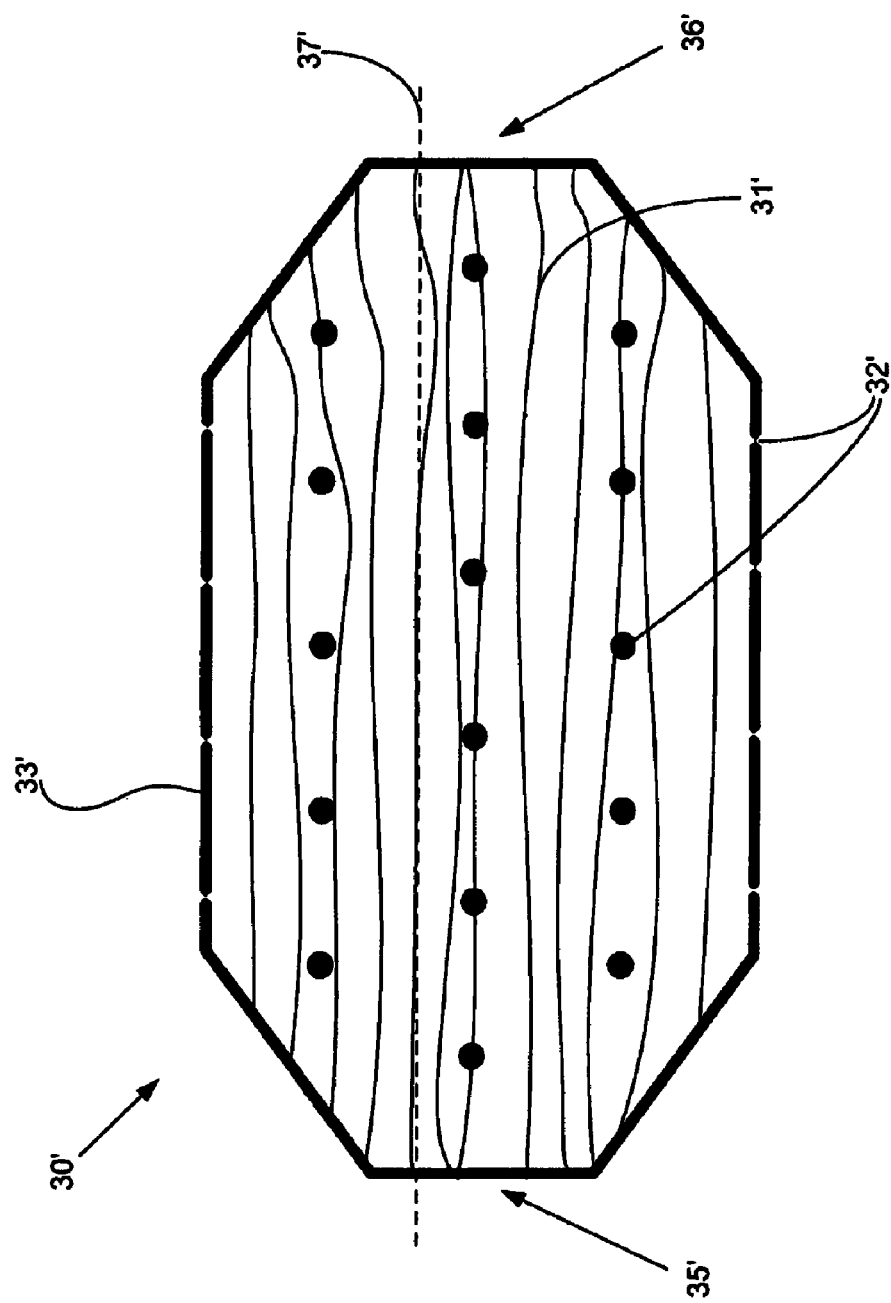
FIG. 2D illustrates a plan view of an alternative embodiment of the nanotube-reinforced balloon of FIG. 2A.

While FIGS. 2A-2C illustrate nanotubes 31 as having an unconstrained alignment relative to balloon 30, nanotubes 31 may alternatively be aligned relative to balloon 30, which can help to inhibit one or more potential modes of tearing of balloon 30. For example, FIG. 2D illustrates an embodiment in which nanotubes 31' are aligned longitudinally relative to balloon 30'. The longitudinal orientation of nanotubes 31' helps to inhibit potential radial modes of tearing of balloon 30'. In another embodiment (not illustrated), nanotubes 31' are aligned radially relative to balloon 30', which helps to inhibit potential longitudinal modes of tearing of balloon 30'.

In the embodiment illustrated in FIG. 2D, at least a subset of nanotubes 31' generally extend between a first end 35' of balloon 30' and a second end 36' of balloon 30'. However, not all of nanotubes 31' need extend the entire distance between first and second ends 35', 36'; for example, some or all of nanotubes 31' may be longitudinally oriented relative to balloon 30' but may only extend a portion of the distance between first and second ends 35', 36'. Even if no nanotubes 31' extend the entire distance between ends 35' and 36', the portion of wall 33' that is adjacent any given pore 32' is still reinforced by aligned nanotubes which inhibit radial tearing of the balloon around that pore 32'. Nanotubes 31' also need not be precisely oriented relative to balloon 30'. For example, the orientation of each individual nanotube 31' may deviate by more than 1%, more than 2%, more than 5%, or even more than 10% from imaginary line 37', which represents an orientation that is exactly longitudinal relative to balloon 30'. Radially aligned nanotubes may have similar length and/or alignment as described for longitudinally aligned nanotubes.

Nanotubes 31' may be aligned longitudinally and/or radially relative to balloon 30' using any suitable technique, e.g., gel spinning or electrospinning. In gel spinning, nanotubes 31' are dispersed within a suitable melted polymer (e.g., as described below with respect to FIG. 5). The melted nanotube/polymer mixture is extruded through a suitably shaped die and the extruded end pulled upon, which causes chains of the polymer and the nanotubes to align substantially parallel to the direction of extrusion. To form balloon 30' having longitudinally oriented nanotubes 31', the die is cylindrically shaped and includes a mandrel for forming a lumen within balloon 30'. To instead form balloon 30' having radially oriented nanotubes 31', the die is shaped to extrude a sheet or ribbon; after extrusion, the sheet or ribbon may be looped into a cylinder and the edges sealed (e.g., with heat and pressure) to form balloon 30'. Electrospinning includes applying an electrical field during extrusion that orients the nanotubes.

Figure 2E:
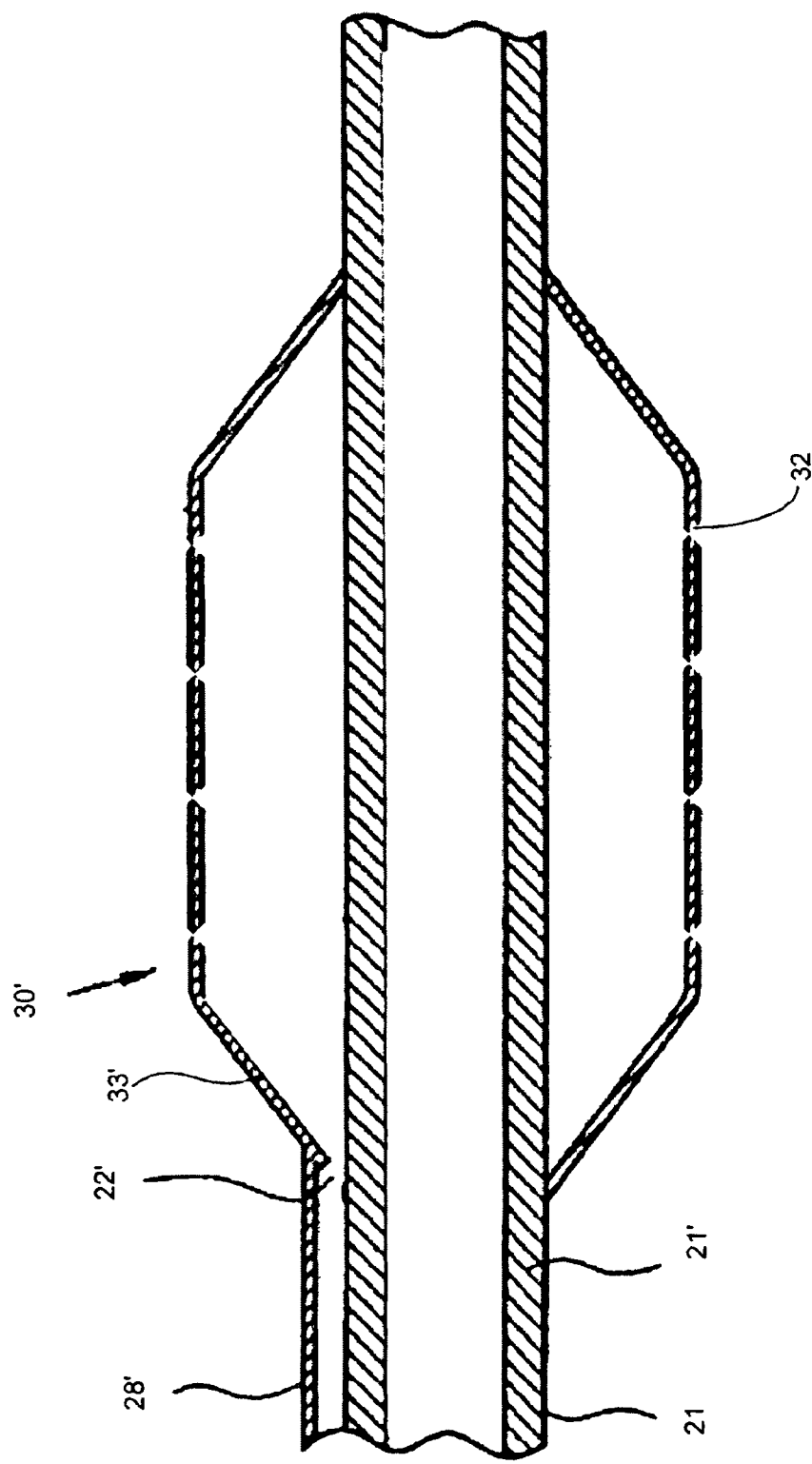
FIG. 2E illustrates a longitudinal sectional view of an alternative embodiment of the nanotube-reinforced balloon of FIG. 2A.

In an alternative embodiment of balloon 30, designated 30" in FIG. 2E, inflation lumen is disposed against wall 21" of shaft 21. Port 22" exists in flexible wall 33", and inflation lumen 28" may pass through port 22" and terminate within balloon 30". Alternatively, the distal end of inflation lumen 28" may be affixed to flexible wall 33" such that it provides communication through port 22".

Figure 3A:
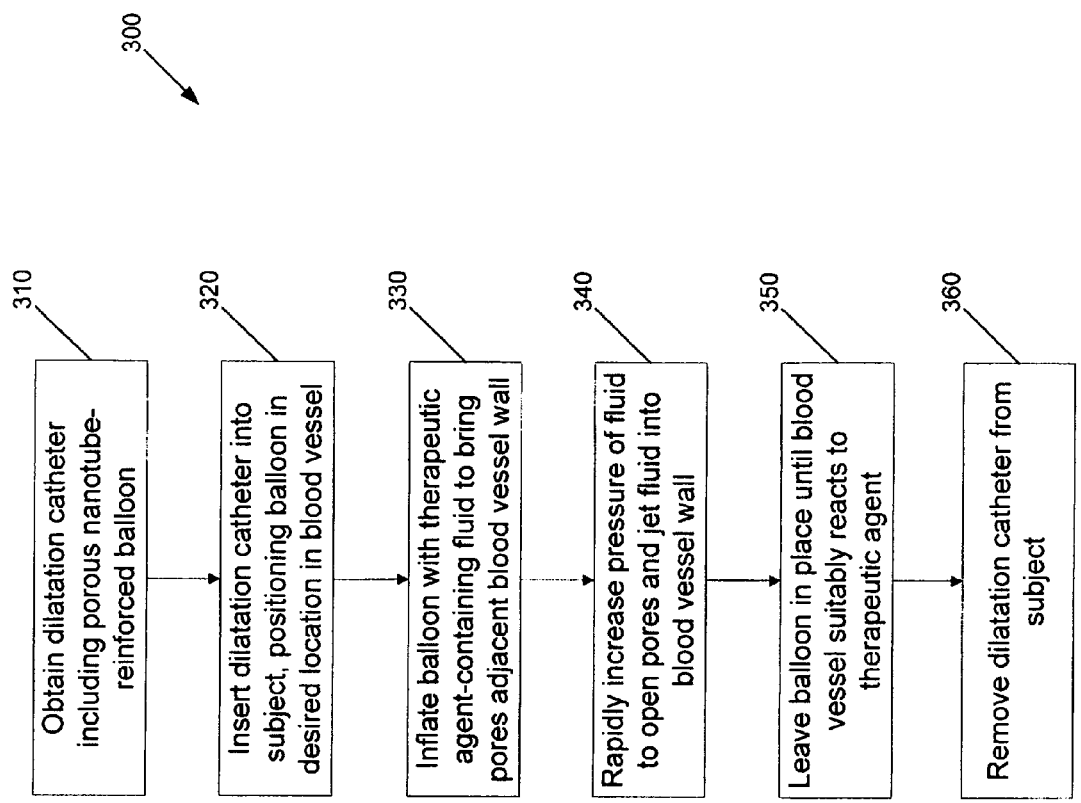
FIG. 3A illustrates a method of delivering a therapeutic agent within a wall of a blood vessel using a nanotube-reinforced balloon, according to one embodiment of the present invention.

FIG. 3A illustrates steps in a method 300 of delivering a therapeutic agent within a wall of a blood vessel using a nanotube-reinforced balloon, according to some embodiments of the present invention. First, a dilatation catheter constructed in accordance with embodiment of the present invention which includes a porous, nanotube-reinforced balloon is obtained (310). In the embodiments illustrated in FIGS. 2A-2C, the balloon is in fluidic communication with a fluid source that contains a therapeutic agent to be delivered within the wall of the blood vessel. The fluid source is configured so that the pressure of the fluid within the balloon may be varied over time from a low pressure sufficient to inflate the balloon and expand the blood vessel while low enough that the pores remain closed, to a high pressure sufficient to open the pores and to jet the therapeutic agent through the pores and into the wall of the blood vessel.

The dilatation catheter is inserted into the subject (320). For example, the dilatation catheter may be inserted into a blood vessel (e.g., vein or artery) of the subject, and positioned at a desired location in the blood vessel (e.g., adjacent a stenotic lesion) using known techniques. Optionally, the therapeutic agent-containing fluid also contains a contrast agent, and the nanotube-reinforced balloon is partially filled with the fluid prior to positioning and then imaged using conventional radiography in order to aid in positioning the balloon.

The balloon of the dilatation catheter then is inflated with the therapeutic agent-containing fluid at a pressure below the predetermined threshold pressure, but sufficient to bring the pores of the balloon adjacent the wall of the blood vessel (330).

The pressure of the fluid is then rapidly increased to at least the predetermined threshold pressure, thus opening the pores of the balloon and jetting fluid through the pores and into the wall of the blood vessel (340). Optionally, the pressure of the fluid is increased to a pressure sufficient that the fluid is delivered beyond the wall of the blood vessel.

After jetting fluid into or beyond the wall of the blood vessel, the balloon optionally may be left inflated in place until the blood vessel at least partially reacts to the therapeutic agent (350). For example, if the therapeutic agent is a cross-linking enzyme for creating an in-situ stent within the blood vessel, the balloon is left inflated in place until the in-situ stent has formed with sufficient strength to hold the blood vessel open after the balloon is removed. The dilatation catheter then is removed from the subject (360).

Figure 3B:
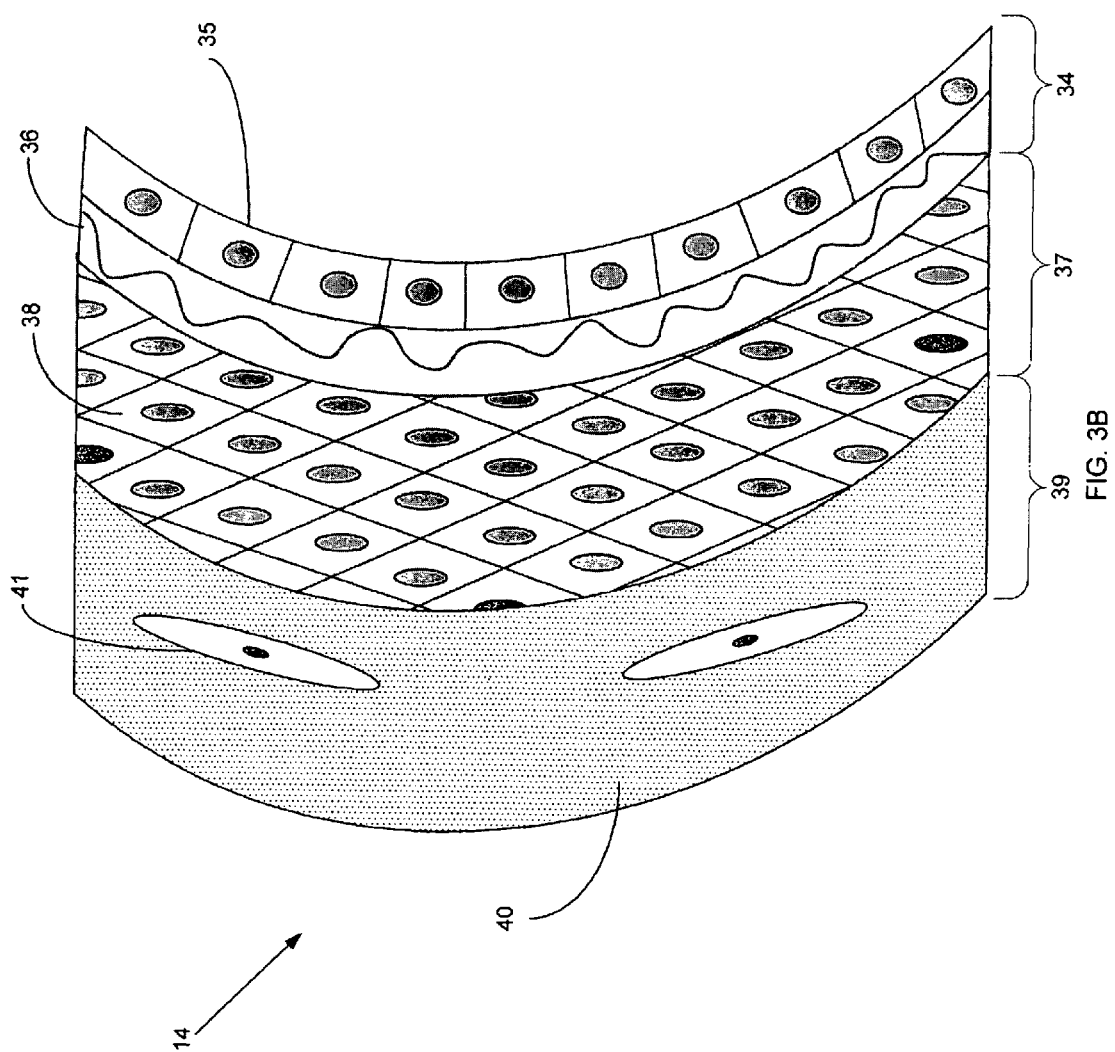
FIG. 3B illustrates a detailed cross-sectional view of the physiological features of an artery.

To aid in better appreciating the different depths to which the therapeutic agent delivered, FIG. 3B illustrates a detailed cross-sectional view of the physiological features of an artery 14. As is familiar to those of skill in the art, artery 14 is considered to have three layers: tunica intima (or "intima") 34, tunica media (or "media") 37, and tunica adventitia (or "adventitia," also referred to as "tunica extema") 39. Intima 34 is the innermost layer of artery 14, and directly contacts the blood. Intima 34 includes endothelial cells 35 which line the lumen of artery 14, and elastica intema 36 that attaches endothelial cells 35 to media 37. Media 37 includes smooth muscle cells 38 and elastic tissue (not shown). Adventitia 39 includes matrix 40 of collagen fibers and vasa vasorum (not shown), as well as fibroblasts 41. By appropriately selecting the pressure of the fluid jetted from the pores of the nanotube-reinforced balloon, the therapeutic agent may be delivered to a desired depth within artery 14, e.g., to one or more of intima 34, to media 37, and/or adventitia 39. For example, the therapeutic agent may be delivered within adventitia 39, which contains blood vessels that themselves supply blood to the artery, thus aiding in distribution of the therapeutic agent to a localized region of the artery. The therapeutic agent may even be delivered outside of adventitia 39, e.g., so that the therapeutic agent contacts or coats the exterior of the wall of artery 14.

Figure 3C:
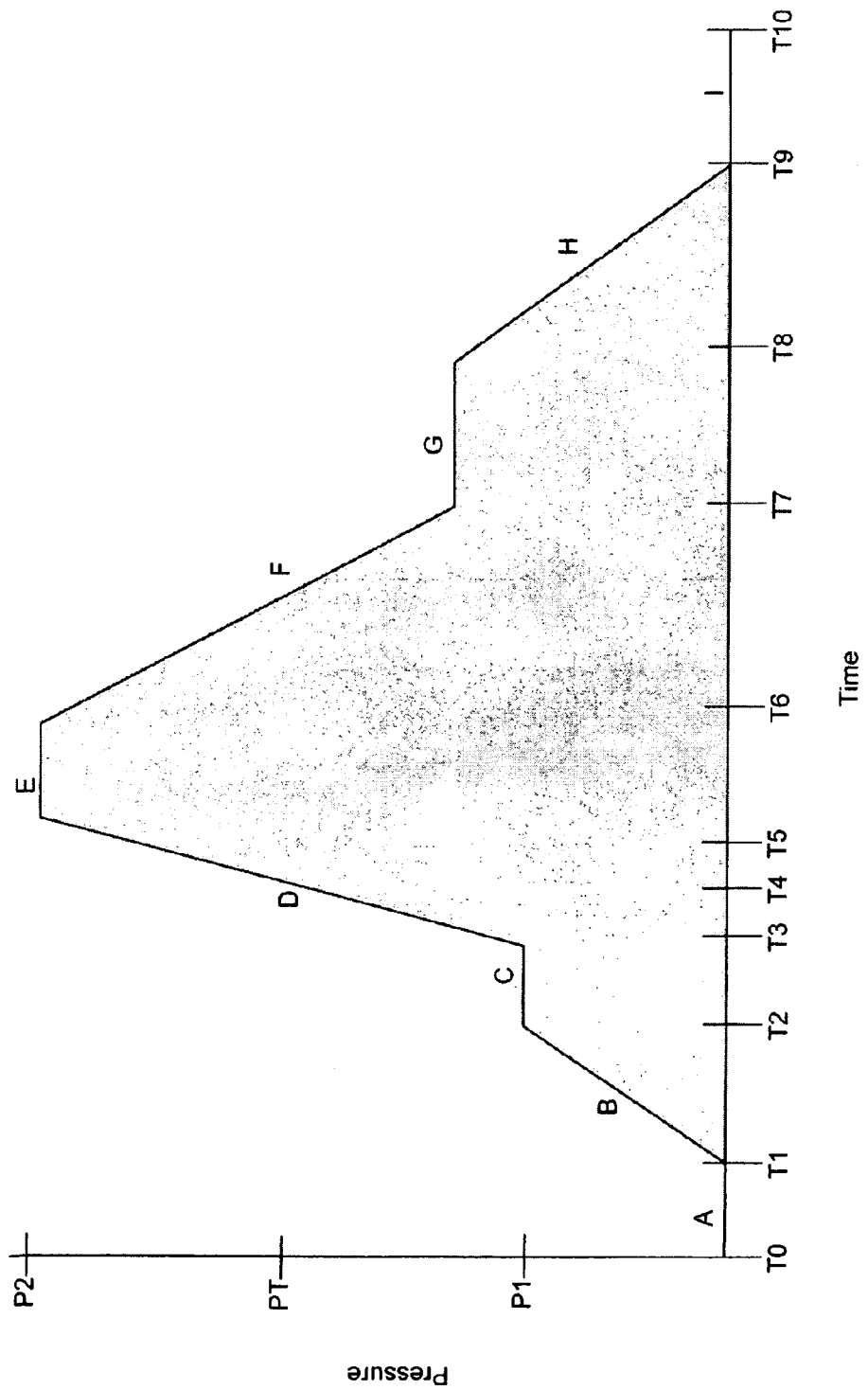
FIG. 3C illustrates an exemplary pressure profile that may be used to inflate a nanotube-reinforced balloon and to deliver a therapeutic agent from pores in the inflated nanotube-reinforced balloon, according to some embodiments of the present invention.

FIG. 3C illustrates an exemplary sequence (A, B, . . . I) of fluidic pressures to which the nanotube-reinforced balloon may be subjected first to inflate the balloon, and then to deliver therapeutic agent into a blood vessel wall from pores in the balloon. The times and pressures illustrated in FIG. 3C are not to scale, and are intended to be merely illustrative. Beginning at an initial time T0, the balloon is positioned within a blood vessel while in a deflated state (A). Optionally, the balloon is partially inflated, at a low and constant pressure, with a fluid containing a contrast agent, and the balloon is imaged using radiography while it is being positioned.

Beginning at time T1, after the balloon has been positioned, the pressure is increased within the balloon up to a pressure P1 that is below the threshold pressure PT at which the pores in the balloon are configured to open (B). At time T2, the pressure P1 has been reached and is held steady (C). Beginning at time T3, the pressure is rapidly increased up to a target pressure P2 that is at least as large as the threshold pressure PT (D). At time T4, when the pressure reaches PT, the pores open. At time T5, the target pressure P2 is reached, and is held steady until time T6 (E). The pressure then is reduced, e.g., as the release of additional fluid from the pores naturally reduces the pressure within the balloon (F). Once the pressure drops just below PT at time T7, the pores stop delivering fluid, which stabilizes the pressure (G). Then, beginning at time T8, the pressure is reduced to withdraw fluid from the balloon (H). Once the balloon is sufficiently or completely deflated at time T9, the balloon is withdrawn from the blood vessel (I). At time T10, the dilatation catheter is withdrawn from the subject.

FIG. 3C is only one example of a sequence of pressures that may be used. For example, the balloon may be pressurized from low pressure to P2 in a single step (thus omitting segment C of the sequence). In some embodiments, after the target pressure P2 is reached, the pressure is not held steady at P2 but is instead allowed to drop (thus omitting segment E of the sequence). In some embodiments, the pores do not re-close when the pressure drops below PT, and so the pressure will not stabilize just below PT (thus omitting segment G of the sequence). Also, the pressure may be smoothly varied over time, instead of linearly as is illustrated in FIG. 3C.

In some embodiments, the inflation pressure P1 is in the range of about 1 atm to 4 atm, or about 1 atm to 3 atm, or about 1 atm to 2 atm, or about 2 atm to 3 atm, or about 2 atm to 4 atm. In some embodiments, one or both of the threshold pressure PT and the target pressure P2 is in the range of about 4 to 16 atm, or about 4 to 8 atm, or about 4 to 6 atm, or about 6 to 8 atm, or about 8 to 16 atm, or about 8 to 12 atm, or about 10 to 12 atm, or about 12 to 16 atm, or about 16 to 18 atm. In some embodiments, the inflation pressure P1 is in the range of about 4 to 10 atm, or about 4 to 8 atm, or about 4 to 6 atm, or about 6 to 10 atm, or about 8 to 10 atm. In some embodiments, one or both of the threshold pressure PT and the target pressure P2 is in the range of about 10 to 35 atm, or 10 to 20 atm, or 15 to 25 atm, or 20 to 30 atm, or 30 to 35 atm). In some embodiments, the initial velocity of the therapeutic agent is in the range of about 200-2500 m/s, with a momentum density in the range of 4-7 kg/s/m.

A variety of mechanisms may be used to controllably vary the pressure within the balloon. FIGS. 3D-3E illustrate pressure-controllable fluid source 27 suitable for use in inflating a nanotube-reinforced balloon and to deliver a therapeutic agent from pores in the inflated nanotube-reinforced balloon. Fluid source 27 includes hollow pressurizer body 380, fluid reservoir 379, and actuator 377. Fluid source also is attached to shaft 21 of dilatation catheter 20 via inflation lumen 28, through which nanotube-reinforced balloon 30 may be controllably inflated and used to deliver therapeutic agents into the wall of a blood vessel (as illustrated in FIG. 2A). Dilatation catheter 20 additionally may include an interface that allows the pressure within inflation lumen 28 to be controlled, e.g., to increase or decrease the pressure of the fluid being applied to balloon 30 and/or to change the rate at which the pressure is varied.

Hollow pressurizer body 380 includes piston 373, which is movable between first position 371 and second position 372. Flexible seal 374 (e.g., an o-ring made of biocompatible polymer) helps create a tight seal between hollow pressurizer body 380 and piston 373 as piston 373 moves between the first and second positions. Fluid reservoir 379 is in fluidic communication with hollow pressurizer body 380 via lumen 378. Fluid reservoir 379 includes a fluid that contains a therapeutic agent, and optionally also contains a contrast agent. Actuator 377 is operably coupled to piston 373 and may be, for example, a pressurized cartridge of gas (e.g., $CO_2$), a spring, a hand pump, or an Indeflator (Abbott Laboratories, Abbott Park, Ill.).

As is illustrated in FIG. 3D, piston 373 moves from first position 371 to second position 372 to draw fluid from fluid reservoir 379 through lumen 378 and into hollow pressurizer body 380. Fluidic communication between pressurizer body 380 and inflation lumen 28 may be temporarily disabled using a valve (not shown) while hollow pressurizer body 380 is filled with fluid. In one embodiment, piston 373 moves from first position 371 to second position 372 responsive to actuation by actuator 377. Here, actuator 377 moves piston 373 from the first position to the second position, creating a vacuum in hollow pressurizer body 380 that draws fluid from fluid reservoir 379 through lumen 378. In another embodiment, piston 373 moves from first position 371 to second position 372 responsive to pressurization of fluid reservoir 379. Here, vent 375 provides a fluidic pathway for gas in pressurizer body 380 to escape as pressurized fluid moves from fluid reservoir 379 and into pressurizer body 380 though lumen 378.

As is illustrated in FIG. 3E, piston 373 moves from second position 372 to first position 371 responsive to actuation by actuator 377, to deliver fluid from hollow pressurizer body 380 into nanotube-reinforced balloon 30 via inflation lumen 28. Fluidic communication between pressurizer body and 380 and fluid reservoir 379 may be temporarily disabled using a valve (not shown) while fluid is delivered to nanotube-reinforced balloon 30. The pressure, and rate of pressure increase, that piston 373 creates in the fluid is based at least in part on the force and rapidity with which piston 373 moves to first position 371 responsive to actuator 377. The piston may be moved mechanically, pneumatically, hydraulically, piezo-electrically, or otherwise, into the first position.

Note that fluid reservoir 379 and shaft 21 need not be simultaneously connected to pressurizer body 380. For example, pressurizer body 380 may include a single connector connects either to fluid reservoir 379 or to shaft 21.

Actuator 377 may be manual, automatic, or partially automatic. For example, actuator 377 may automatically actuate piston 373 to first move at a rate and with a force sufficient to inflate the nanotube-reinforced balloon to a first pressure below the threshold pressure (P1), and then to move at a rate and with a force sufficient to open the pores in the balloon and deliver the drug to a defined distance in the wall of the blood vessel (P2). Or, for example, the balloon may be manually inflated using conventional methods to a first pressure below the threshold pressure (P1), optionally using feedback from radiography, and actuator 377 then actuated to automatically increase the pressure to open the pores and deliver the drug to the wall of the blood vessel (P2). Or, for example, the balloon may be manually inflated, and then the pressure manually adjusted above the threshold pressure (to P2) by controlling one or more settings of actuator 377.

Other types of pressure-controllable fluid sources 27 may be used. For example, the balloon may be conventionally pressurized to a pressure below the threshold pressure (P1). However, a separate lumen in fluidic communication with the balloon may be provided that may be rapidly pressurized, e.g., using a $CO_2$ cartridge or other sonic energy delivery system.

Figure 4A:
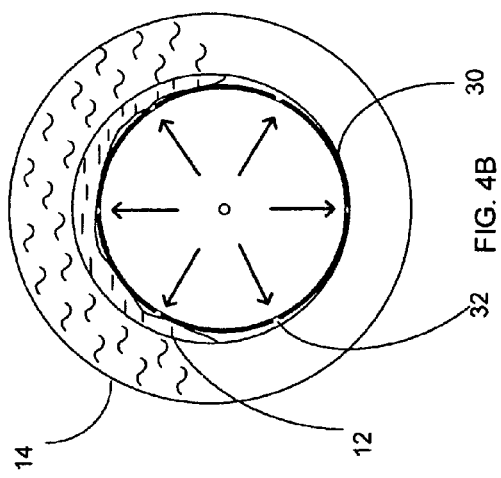
FIG. 4A illustrates a cross-sectional view of a deflated, nanotube-reinforced balloon positioned adjacent a stenotic lesion in an artery, according to some embodiments of the present invention.
Figure 4B:
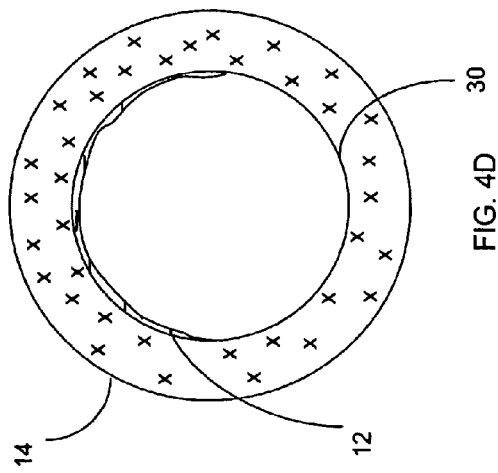
FIG. 4B illustrates a cross-sectional view of an inflated, nanotube-reinforced balloon compressing a stenotic lesion in an artery, according to some embodiments of the present invention.

FIGS. 4A-4D illustrate cross-sectional views of the treatment of artery 14 using the nanotube-reinforced balloon 30 described above with reference to FIGS. 2A-2C. As illustrated in FIG. 4A, balloon 30 is positioned so that it traverses or crosses stenotic lesion 12 within the artery 14. As is illustrated in FIG. 4B, balloon 30 then is inflated with a therapeutic agent-containing fluid at relatively low pressures. This fluid compresses balloon 30 against lesion 12, and dilates artery 14 in a direction generally perpendicular to its wall, thereby dilating the lumen of the artery. During inflation of balloon 30, the pressure of the fluid is kept below the predetermined threshold pressure at which pores 32 are configured to open.

Figure 4C:
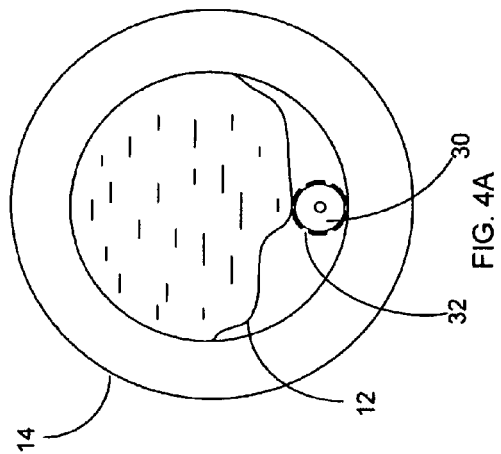
FIG. 4C illustrates a cross-sectional view of an inflated, nanotube-reinforced balloon delivering a fluidic therapeutic agent within an arterial wall, according to some embodiments of the present invention.

As is illustrated in FIG. 4C, after pores 32 are brought adjacent to the wall of artery 14, the pressure is then rapidly increased within balloon 30 to above the predetermined threshold pressure, causing pores 32 to open. As illustrated by the arrows, the pores emit the therapeutic agent-containing fluid from the interior of balloon 30 and into (or even beyond) the wall of artery 14. The balloon may be held in place for an amount of time selected to allow the therapeutic agent to suitably react with the wall of artery 14. For example, in embodiments in which the therapeutic agent forms an in-situ stent, the amount of time is selected to allow the therapeutic agent to sufficiently enhance the mechanical properties of the wall of artery 14 such that the artery is not susceptible to recoil or restenosis. Or for example, in embodiments in which the therapeutic agent is an antiproliferative drug, the balloon need not be held in place and may simply be removed.

Figure 4D:
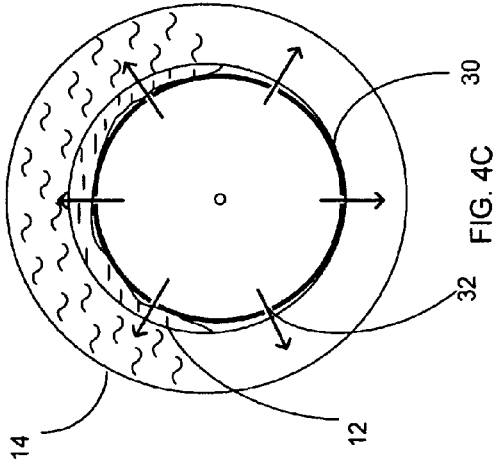
FIG. 4D illustrates a cross-sectional view of an artery following delivery of a fluidic therapeutic agent within the arterial wall using a nanotube-reinforced balloon, according to some embodiments of the present invention.

FIG. 4D illustrates artery 14 following treatment with the therapeutic agent and withdrawal of balloon 30. In the illustrated embodiment, the mechanical properties of the wall of artery 14 have been enhanced (illustrated as "x") to form an in-situ stent. While a small amount of tissue proliferation 12' may occur, artery 14 is significantly more patent and stable than following conventional PTCA, as illustrated in FIG. 1C.

FIG. 5 illustrates a method 500 of forming the nanotube-reinforced balloon of FIGS. 2A-2C, according to some embodiments. First, nanotubes are acquired (510), for example from commercially available sources, or are fabricated. The nanotubes may include single-walled carbon nanotubes (SWNT) and/or multi-walled carbon nanotubes (MWNT). The carbon nanotubes may include conducting and/or semiconducting nanotubes. The carbon nanotubes may be "pristine," that is, not functionalized, derivitized, or otherwise modified (e.g., including substantially no atoms other than carbon). Alternatively, one or more of the carbon nanotubes may be functionalized or derivitized to have desired therapeutic properties, or to enhance their dispersion in the polymer.

Other types of materials may be used in the balloon, either in addition to the nanotubes, or instead of the nanotubes. For example, inorganic nanotubes (e.g., tungsten disulfide, boron nitride, silicon, titanium dioxide, molybdenum disulfide, copper, or bismuth nanotubes) may be used to reinforce the flexible wall of the balloon. Or, for example, graphene fibers may be used to reinforce the flexible wall of the balloon. Or, for example, fibers of Kevlar (poly paraphenylene terephthalamide), Teflon (polytetrafluoroethylene), Terlon (poly(p-phenylenebenzobisthiazole)), Zylon (poly(p-phenylene-2,6-benzobisozazoles), polyether block amides, and Vectran (liquid crystal polymer) may be used to reinforce the flexible wall of the balloon. The selected material(s) must sufficiently strengthen the balloon that pressurizing the balloon to a pressure at or above the threshold pressure of the pores defined therein does not tear the pores or the balloon.

A suitable polymer is then heated above its melting point (520). Suitable polymers include polyester, polyolefin, fluoropolymers such as polytetrafluoroethylene (PTFE, trade name Goretex), nylon, urethanes, polyurethane, polyvinyl chloride (PVC), polyethylene terephthalate (PET, trade name Dacron, DuPont, Wilmingon Del.), polyethylene naphthalate, polybutylene naphthalate, polyethylene, polypropylene, polyimides, polyamides such as Pebax, or other polymer that is biocompatible, in which nanotubes disperse, and which has suitable mechanical properties, when mixed with nanotubes, to form a balloon that may withstand rapid pressurization. Examples of some suitable polymers may be found in U.S. Pat. No. 5,871,468, entitled "Medical Catheter With a High Pressure/Low Compliant Balloon," the entire contents of which are incorporated herein by reference. Copolymers of tetrafluoroethylene with ethylene, cholorotrifluoroethylene, perfluoroalkoxytetrafluoroethylene, or fluorinated propylenes such as hexafluoropropylene also may be used.

The nanotubes then are mixed into the melted polymer while the polymer is maintained at a temperature above its melting point (530). The nanotubes are added to the polymer in an amount sufficient for the balloon formed of the polymer-nanotube mixture to have sufficient mechanical properties to withstand rapid pressurization. For example, the nanotubes may be added to the polymer in an amount of less than about 5% w/w, or less than about 4% w/w, or less than about 3% w/w, or less than about 2% w/w, or less than about 1% w/w, or less than about 0.5% w/w, or less than about 0.25% w/w, or less than about 0.1% w/w.

The nanotubes then are thoroughly and substantially evenly distributed (dispersed) throughout the polymer (540), forming a polymer/nanotube solution. This may be accomplished using mechanical agitation, for example, using an ultrasonic homogenizer (sonicator), using a material compounder, moving a container holding the polymer/nanotube solution, stirring the polymer/nanotube solution, or by maintaining the polymer/nanotube solution above the polymer melting temperature for an extended period of time.

Those of skill in the art will recognize that nanotubes tend to "clump" together due to van der Waals forces and other attractive forces, and thus may form "nanoropes" made up of bundles of nanotubes. The polymer/nanotube solution may therefore include one or more of such nanoropes. While in many embodiments the solution includes a relatively even distribution of nanotubes, the presence of an occasional nanorope is not believed to detrimentally affect the properties of the nanotube-reinforced balloon eventually formed from the solution. Some embodiments include a relatively even distribution of nanoropes in the polymer.

Once the nanotubes are distributed in the polymer to a satisfactory degree, the polymer/nanotube solution is allowed to cool (550), forming a polymer/nanotube composition. The nanotube-reinforced balloon then is formed from the composition (560), for example, by extruding the composition. It should be understood that prior to forming the balloon, the polymer/nanotube composition is optionally pelletized and re-extruded or otherwise formed using known techniques.

Next, pores are formed in the nanotube-reinforced balloon (570). The pores may be circular, oval square, slits, or conical, for example. The pores may be formed by irradiating selected regions of the wall with an appropriately focused laser. Alternatively, the pores may be formed by lightly pricking the balloon with a pin. As a further alternative, microbubbles may be formed in the wall of the balloon (e.g., by appropriately mixing air into the composition during step 550), and the microbubbles destroyed (e.g., by sonicating the balloon) at step 570 to form pores. Mechanical punching, mechanical drilling, ion-beam drilling, electron beam drilling, and other techniques may also be used, provided that they form pores of appropriate size and characteristics such that the therapeutic agent does not leak from the balloon below a predefined threshold pressure.

The nanotube-reinforced balloon then is affixed to the shaft of a dilatation catheter (580) such that the balloon is in fluidic communication with a pressurized source of fluid that contains a suitable therapeutic agent.

Optionally, other parts of the dilatation catheter may be formed of the polymer/nanotube composition. For example, the composition may be used to form shaft 21 of dilatation catheter 20 illustrated in FIG. 2A. Nanotubes, if used in shaft 21, may provide increased axial strength and pushability to dilatation catheter 20, thereby allowing shaft 21 to be produced with reduced dimensions, while at the same time reducing the likelihood of kinking, binding, or similar problems that may conventionally accompany the reduction in dimensions of dilatation catheter parts. Or, for example, the nanotubes may provide "steerability" to shaft 21 and/or guide wire 26. For further details, see U.S. patent Ser. No. 11/267, 226, filed Nov. 3, 2005 and entitled "Radiopaque-Balloon Dilatation catheter and Methods of Manufacture," the entire contents of which are incorporated by reference herein. The type of nanotube and the type of polymer used in balloon 30, and in other parts of dilatation catheter 20, may be selected independently of one another.

In embodiments in which both nanotube-reinforced balloon 30 and shaft 21 are made using a nanotube-polymer mixture, the nanotubes may be used to enhance bonding between balloon 30 and shaft 21. Specifically, nanotubes have a propensity to lock together when brought near each other. Nanotube-reinforced balloon 20 and shaft 21 may be bonded together using a technique that allows the nanotubes in the two components to lock together, for example, by bringing the two components adjacent each other and then heating the polymer/nanotube composition just higher than the melting point of the polymer. While the polymer is heated, nanotubes in one component may move through the composition and lock together with nanotubes in the other component. Electromagnetic fields optionally may be used to selectively orient the nanotubes and/or enhance the transport of nanotubes from one component to the other.

Figure 6A:
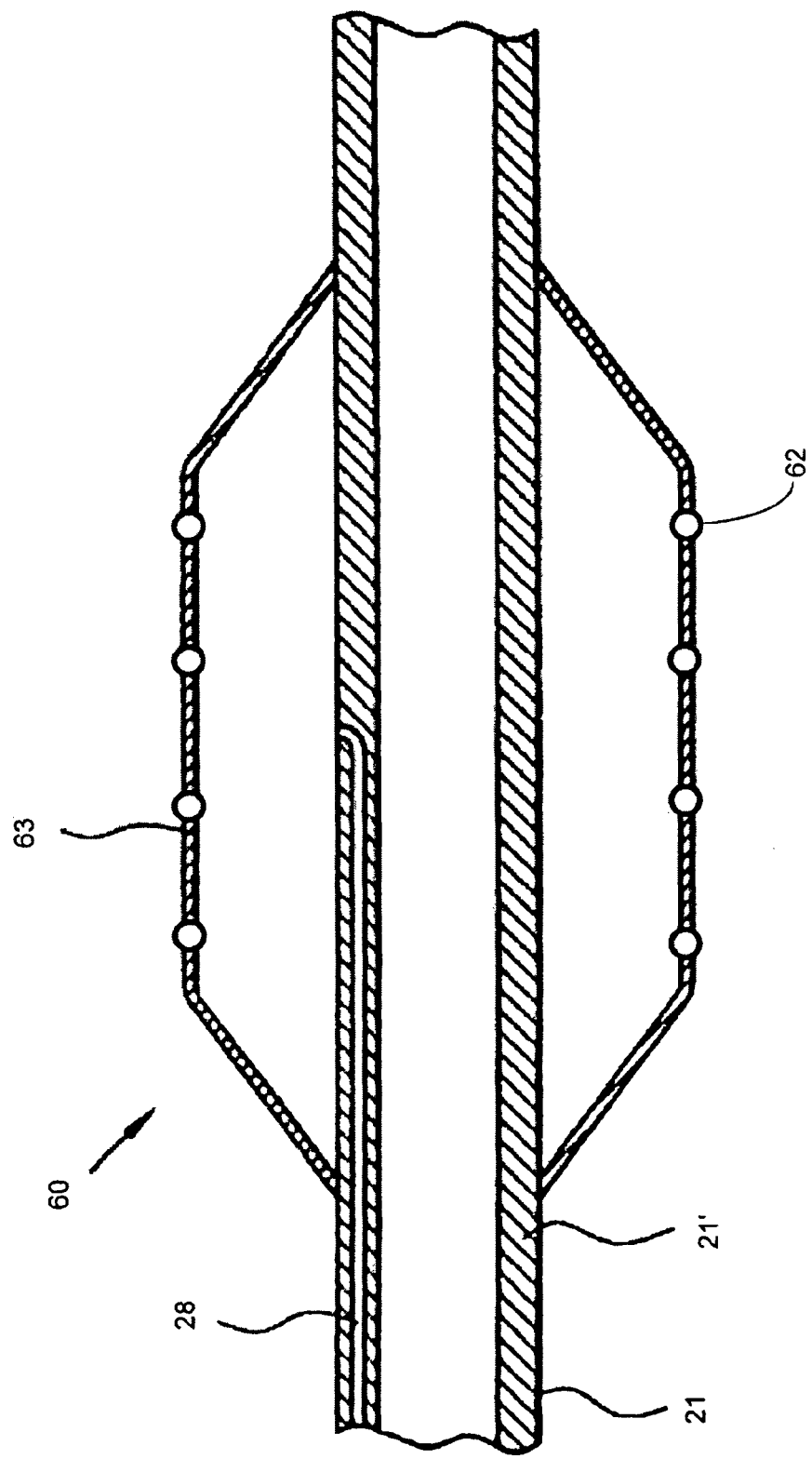
FIG. 6A illustrates a longitudinal sectional view of an alternative embodiment of a nanotube-reinforced balloon, capable of delivering a fluidic therapeutic agent, that may be used in the dilatation catheter of FIG. 2A.

FIG. 6A illustrates a longitudinal sectional view of an alternative embodiment of a nanotube-reinforced balloon that may be used in the dilatation catheter of FIG. 2A. The balloon 60 includes flexible wall 63 affixed to shaft 21. Inflation lumen 28 passes through wall 21' of shaft 21, so that a distal end of inflation lumen 28 communicates with the space defined between the outer surface of shaft 21 and the inner surface of the flexible wall 63. The proximal end of inflation lumen 28 is coupled to inflation port 24. Inflation port 24 is coupled to fluid source 27 (not shown in FIG. 6A) that contains a therapeutic agent, and optionally also a contrast agent, the pressure of which may be controlled.

Flexible wall 63 of nanotube-reinforced balloon 60 are formed from a composition that includes a plurality of carbon nanotubes that are substantially evenly dispersed in a polymeric matrix. A plurality of microbubbles 62 are defined in flexible wall 63 of balloon 60. Microbubbles 62 are configured to remain intact until a pressure within the balloon meets or exceeds a predefined threshold pressure, at which pressure microbubbles 62 rupture and thus provide a fluidic pathway through which fluid inside of balloon 60 may exit as high velocity jets. This feature allows the balloon to first be inflated at a relatively low pressure, bringing microbubbles 62 adjacent the blood vessel wall, and subsequently subjected to a pressure exceeding a predefined threshold pressure, allowing therapeutic agent to jet from the ruptured microbubbles and into the blood vessel wall. As noted above with referenced to FIG. 5, microbubbles 62 may be formed by mixing air into the heated polymer/nanotube solution at step 540, e.g., using a sonicator. The size and density of microbubbles may be controlled, for example, by adjusting the frequency of sonication and the amount of time the solution is subjected to sonication.

Figure 6B:
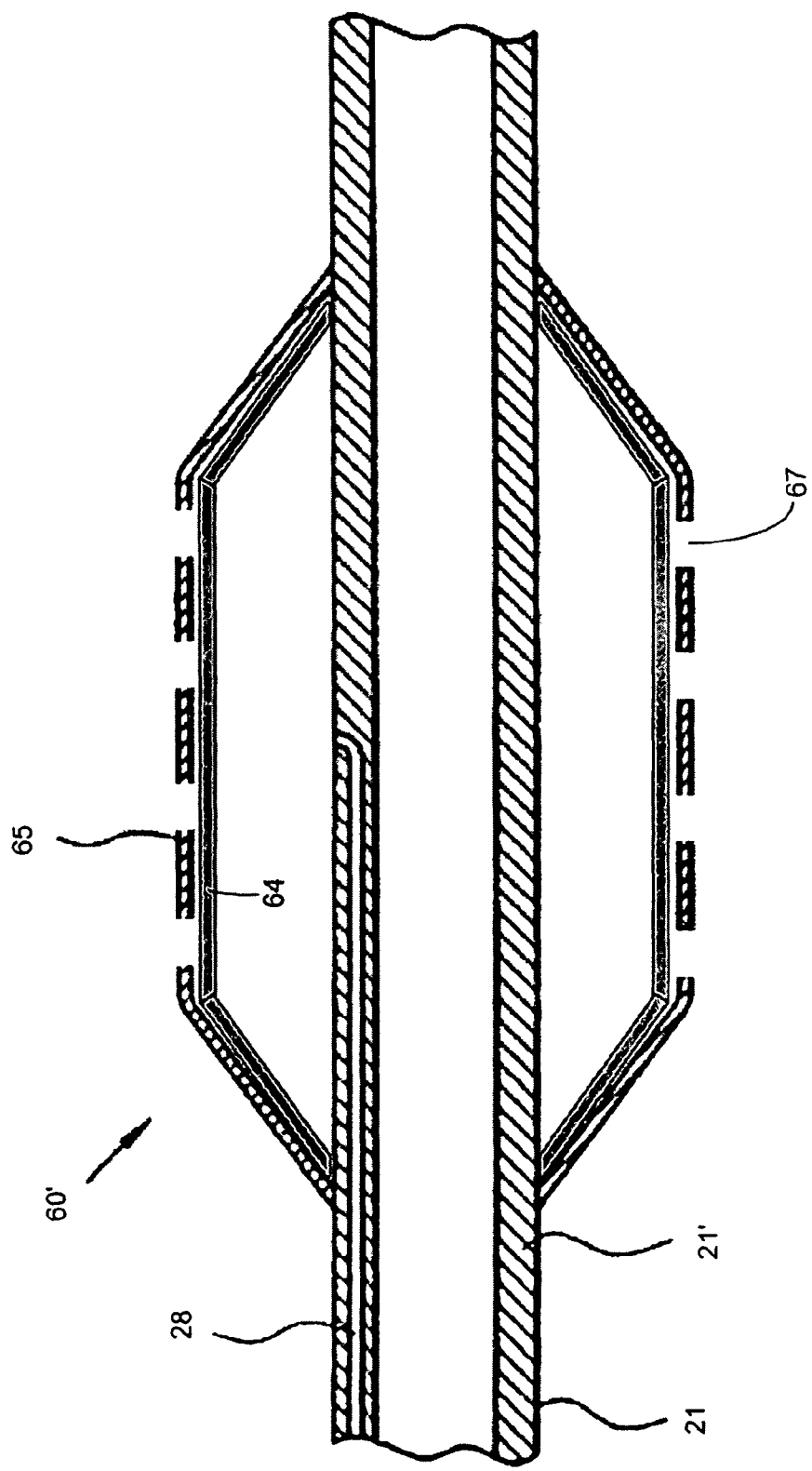
FIG. 6B illustrates a longitudinal sectional view of another alternative embodiment of a nanotube-reinforced balloon, capable of delivering a fluidic therapeutic agent, that may be used in the dilatation catheter of FIG. 2A.

FIG. 6B illustrates a longitudinal sectional view of another alternative embodiment of a nanotube-reinforced balloon that may be used in the dilatation catheter of FIG. 2A. The balloon 60' include inner flexible wall 64 and outer flexible wall 65, affixed to shaft 21. Inflation lumen 28 passes through wall 21' of shaft 21, so that a distal end of inflation lumen 28 communicates with the space defined between the outer surface of shaft 21 and the inner surface of the inner flexible wall 64. The proximal end of inflation lumen 28 is coupled to inflation port 24. Inflation port 24 is coupled to fluid source 27 (not shown in FIG. 6B) that contains a therapeutic agent, and optionally also a contrast agent, the pressure of which may be controlled.

At least one of inner flexible wall 64 and outer flexible wall 65 of nanotube-reinforced balloon 60' is formed from a composition that includes a plurality of carbon nanotubes that are substantially evenly dispersed in a polymeric matrix. Outer flexible wall 65 is stronger (e.g., has a higher elastic modulus) than inner flexible wall 64. Inner flexible wall may be made, for example, of a composition including polyisoprene. Pores 67 are defined in outer flexible wall 65, and do not emit fluid until the pressure within the balloon meets or exceeds a predefined threshold pressure, at which pressure inner flexible wall 64 fails. Fluid then jets from inside of balloon 60' through pores 67. This feature allows the balloon to first be inflated at a relatively low pressure, bringing pores 67 in outer flexible wall 65 adjacent the blood vessel wall, and subsequently subjected to a pressure exceeding a predefined threshold pressure, allowing therapeutic agent to jet from pores 67 and into the blood vessel wall.

Balloon 60' may be partially fabricated using the method of FIG. 5, but including additional steps for fabricating inner flexible wall 64 and attaching inner flexible wall to outer flexible wall 65. Both inner flexible wall 64 and outer flexible wall 65 may be independently fabricated using steps 510-560 of method 500. However, the polymers used and the amount of nanotubes distributed in the polymers (if any) for the inner and outer wall may be different from one another, thus resulting in different elastic properties. Then, step 570 is applied only to outer flexible wall 65, forming pores 67. Outer flexible wall 65 is then disposed on inner flexible wall 64, for example by inserting a balloon formed using inner flexible wall 64 inside of a balloon formed using outer flexible wall 65. The two balloons are optionally bonded to each other, e.g., by raising the temperature above the melting point of the polymer used in one or both of the balloons, or by applying an adhesive between the two balloons before inserting the inner balloon into the outer balloon.

In an alternative embodiment of balloon 60' (not illustrated), inner flexible wall 64 has pores defined therein, and outer flexible wall 65 does not include pores. Inner flexible wall 64 is stronger than outer flexible wall 65. The pores defined in inner flexible wall 64 do not emit fluid until the pressure within the balloon meets or exceeds a predefined threshold pressure, and which pressure outer flexible wall 65 fails. Fluid then jets from inside of the balloon through the pores defined in inner flexible wall 64. This alternative embodiment may be fabricated as described above for balloon 60', but forming pores in inner flexible wall 64 instead of in outer flexible wall 65.

As noted above, in some embodiments the nanotube-reinforced balloon is instead configured to eject a solid therapeutic agent into the wall of a blood vessel. FIG. 7A illustrates an embodiment of such a nanotube-reinforced balloon that may be used in the dilatation catheter of FIG. 2A. Nanotube-reinforced balloon 70 includes flexible wall 73 affixed to shaft 21. Inflation lumen 28 passes through wall 21' of shaft 21, so that a distal end of inflation lumen 28 communicates with the space defined between the outer surface of shaft 21 and the inner surface of the flexible wall 73. The proximal end of inflation lumen 28 is coupled to inflation port 24. In this embodiment, inflation port 24 is coupled to fluid source 27 (not shown in FIG. 7A) that, unlike the fluid-delivering devices of FIGS. 2B-2D and 6A-6B, need not contain a therapeutic agent, because the fluid is not delivered to the blood vessel wall. Optionally, fluid source 27 includes a contrast agent.

Figure 7B:
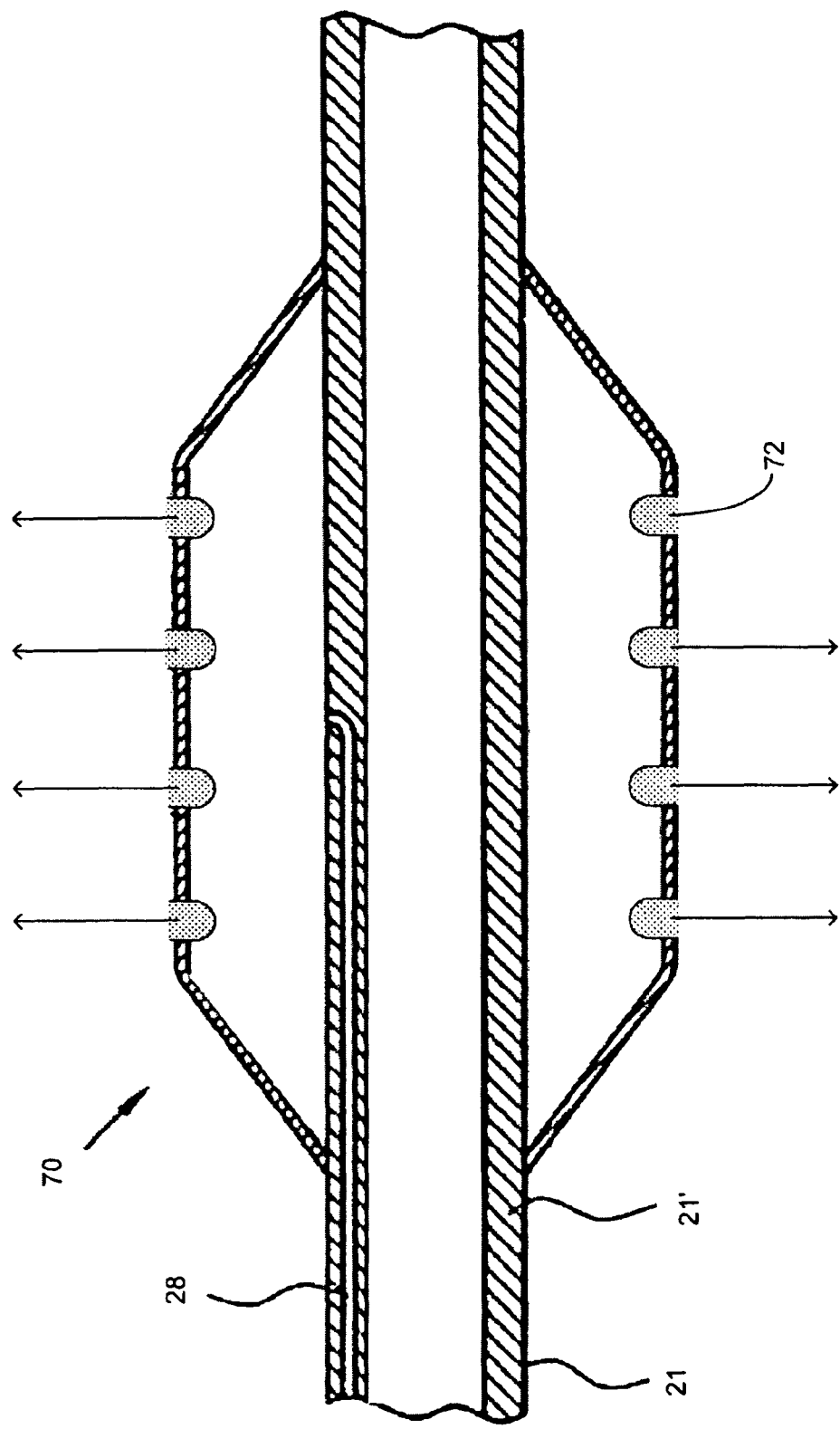
FIG. 7B illustrates the nanotube-reinforced balloon of FIG. 7A while ejecting the solid therapeutic agent.

Flexible wall 73 of nanotube-reinforced balloon 70 is formed from a composition that includes a plurality of carbon nanotubes 31 that are substantially evenly dispersed in a polymeric matrix. Sacs 72 are defined in flexible wall 73 of balloon 70 and/or are attached to flexible wall 73 of balloon 70. Each sac includes an interior portion 74 that contains a particulate therapeutic agent, and an exterior portion 75 that may be substantially the same as the pores described above with reference to FIGS. 2B-2D and 6A-6B. The pores are configured so as to remain closed until a pressure within the balloon meets or exceeds a predefined threshold pressure. This feature allows the balloon to first be inflated at a relatively low pressure in order to bring the pores into a position adjacent a stenotic lesion, without the pores opening. As illustrated in FIG. 7B, when the pressure of the fluid within balloon 70 exceeds the predefined threshold pressure, pores 75 open and the particulate therapeutic agent is ejected from interior portions 74 of sacs 72 to the exterior of balloon 70.

Nanotube-reinforced balloon 70 may be fabricated using steps 510-580 described above with reference to FIG. 5 for fabricating the balloons of FIGS. 2B-2C, but including additional steps for forming sacs 72 containing a particulate therapeutic agent and attaching such sacs to flexible wall 73. Such sacs may be formed, for example, using microencapsulation techniques known in the art, and the sacs then affixed to flexible wall 73 using an adhesive or by raising wall 73 above the melting point of the polymer and then contacting the sacs to wall 73. Or, for example, such sacs may be defined directly within flexible wall 73 using the microbubble techniques described above, and the microbubbles then filled with the therapeutic agent.

Figure 8A:
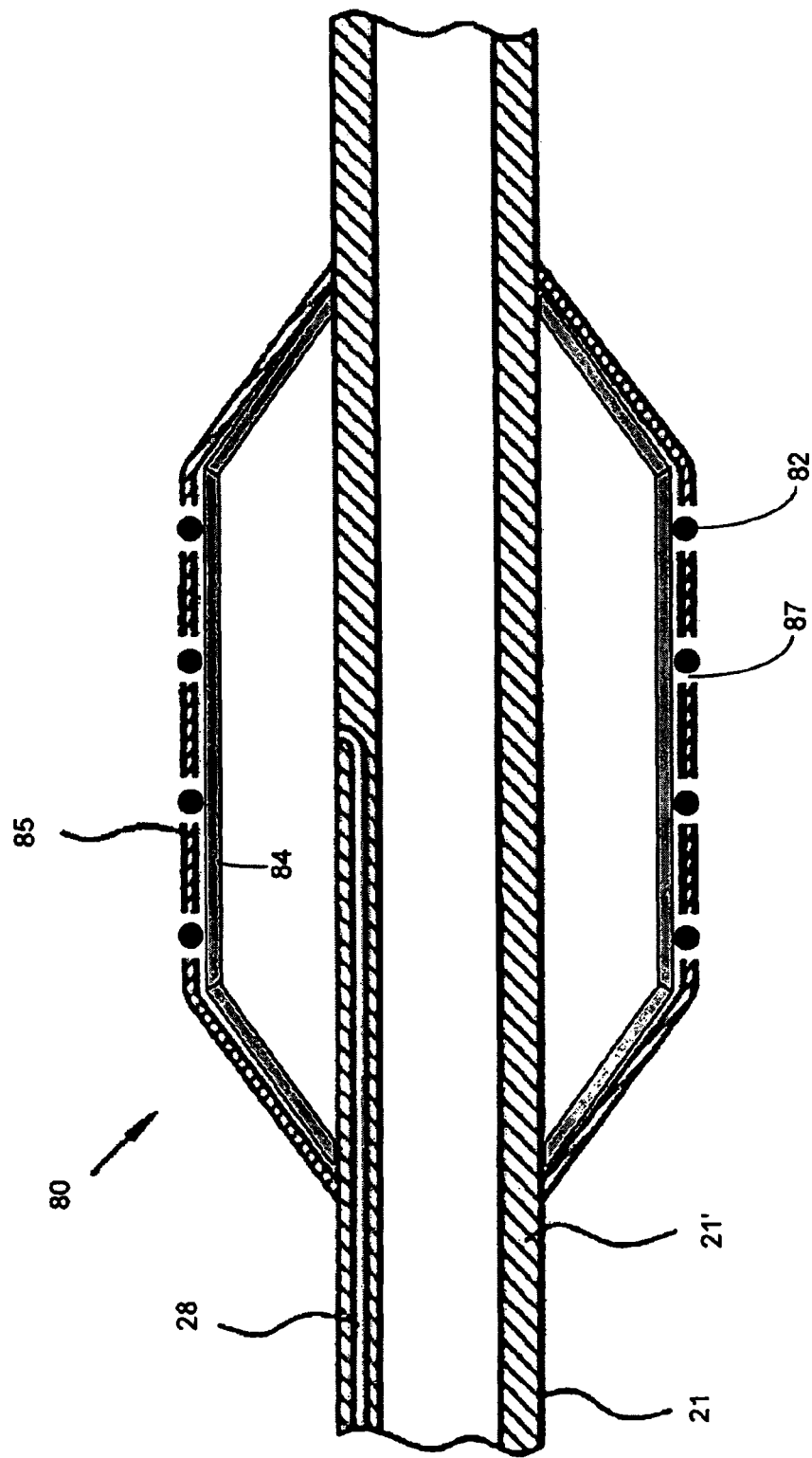
FIG. 8A illustrates a longitudinal sectional view of an alternative embodiment of a nanotube-reinforced balloon, capable of delivering a solid therapeutic agent, that may be used in the dilatation catheter of FIG. 2A.

FIG. 8A illustrates a longitudinal sectional view of an alternative embodiment of a nanotube-reinforced balloon that may be used in the dilatation catheter of FIG. 2A, and that ejects a particulate therapeutic agent. Balloon 80 includes inner flexible wall 84 and outer flexible wall 85, affixed to shaft 21. Inflation lumen 28 passes through wall 21' of shaft 21, so that a distal end of inflation lumen 28 communicates with the space defined between the outer surface of shaft 21 and the inner surface of the inner flexible wall 84. The proximal end of inflation lumen 28 is coupled to inflation port 24. Inflation port 24 is coupled to fluid source 27 (not shown in FIG. 8A) that contains a therapeutic agent, and optionally also a contrast agent, the pressure of which may be controlled.

At least one of inner flexible wall 84 and outer flexible wall 85 of nanotube-reinforced balloon 80 is formed from a composition that includes a plurality of carbon nanotubes that are substantially evenly dispersed in a polymeric matrix. Outer flexible wall 85 is stronger (e.g., have a higher elastic modulus) than inner flexible wall 84. A plurality of pores 87 are defined in outer flexible wall 85, and contain particulate therapeutic agent 82. However, particulate therapeutic agent 82 is not delivered until the pressure within the balloon meets or exceeds a predefined threshold pressure, at which pressure inner flexible wall 84 fails, thus emitting the fluid within the balloon which propels particulate therapeutic agent 82 into the wall of blood vessel. Alternatively, at the predefined threshold pressure the inner flexible wall rapidly flexes outward, thus propelling particulate therapeutic agent 82 into the wall of the blood vessel.

Optionally, pores 87 and/or the outer surface of inner flexible wall 84 have an affinity for particulate therapeutic agent 82 that is sufficiently strong to bind agent 82 within pores 87 until agent 82 is are ejected into the blood vessel. For example, if agent 82 is lipophilic, then pores 87 and/or the outer surface of inner flexible wall 84 may be fabricated so that they are lipophilic, and thus attract agent 82. Or, for example, if agent 82 is hydrophilic, then pores 87 and/or the outer surface of inner flexible wall 84 may be fabricated so that they are hydrophilic, and thus attract agent 82. Such an affinity between agent 82 and pores 87 and/or wall 84 allows agent 82 to be inserted within pores 87 by simply dipping balloon 80 into a reservoir containing particles 82. Such an insertion may be performed at any time before inserting balloon 80 into the subject, even immediately prior to inserting balloon 80 into the subject. In embodiments in which particulate therapeutic agent 82 is radioactive, as described below, inserting agent 82 into pores 87 immediately prior to inserting balloon 80 into the subject is useful because it obviates the need to construct balloon 80 in a facility equipped to handle radiation, and also reduces the amount of radioactive decay experienced by the particles between time of fabrication and time of insertion.

Balloon 80 illustrated in FIG. 8A may be fabricated similarly to balloon 60' illustrated in FIG. 6A, but including an additional step of disposing a therapeutic agent within pores 87.

Figure 8B:
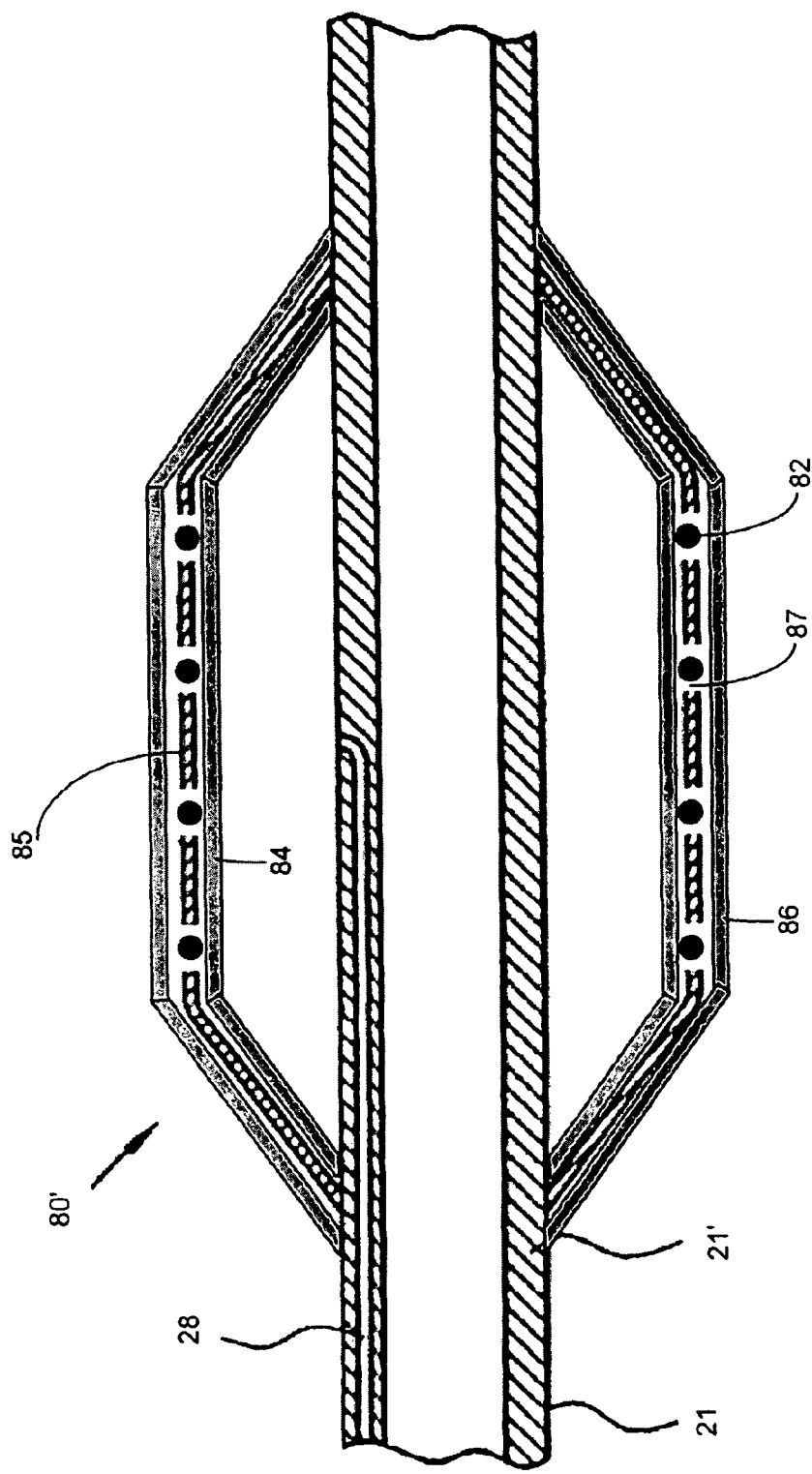
FIG. 8B illustrates a longitudinal sectional view of another alternative embodiment of a nanotube-reinforced balloon, capable of delivering a solid therapeutic agent, that may be used in the dilatation catheter of FIG. 2A.

FIG. 8B illustrates a longitudinal sectional view of another alternative embodiment of a nanotube-reinforced balloon that may be used in the dilatation catheter of FIG. 2A, and that ejects a particulate therapeutic agent. Balloon 80' is substantially the same as balloon 80, including inner flexible wall 84 and outer flexible wall 85 having a plurality of pores 87 defined therein that contain particulate therapeutic agent 82. Balloon 80' also includes a protective outer layer 86 that encapsulates pores 87 and prevents therapeutic agent 82 from falling out of pores 87 until appropriate actuation of the balloon.

At least one of inner flexible wall 84, outer flexible wall 85, and protective layer 86 of nanotube-reinforced balloon 80' is formed from a composition that includes a plurality of carbon nanotubes that are substantially evenly dispersed in a polymeric matrix. Outer flexible wall 85 is stronger (e.g., has a higher elastic modulus) than inner flexible wall 84. Protective layer 86 is weaker (e.g., has a lower elastic modulus) than both outer flexible wall 85 and inner flexible wall 84. Particulate therapeutic agent 82 is not delivered until the pressure within the balloon meets or exceeds a predefined threshold pressure, at which pressure inner flexible wall 84 fails, thus emitting the fluid within the balloon which propels particulate therapeutic agent 82 through protective layer 86 and into the wall of blood vessel. Alternatively, at the predefined threshold pressure the inner flexible wall rapidly flexes outward, thus propelling particulate therapeutic agent 82 through protective layer 86 and into the wall of the blood vessel.

Balloon 80' illustrated in FIG. 8B may be fabricated similarly to balloon 80 illustrated in FIG. 8A, but including an additional step of disposing protective layer 86 over outer flexible wall 85 after therapeutic agent 82 is disposed in pores 87. Protective layer 86 may be disposed over outer flexible wall 85 by, for example, spray coating, dip coating, laminating, powder coating followed by anneal, and the like. Alternatively, an additional balloon formed using protective layer 86 may be formed using steps 510-560 illustrated in FIG. 5 (optionally omitting the addition of nanotubes to the polymer), and said additional balloon applied over a balloon formed using outer flexible wall 85.

A variety of therapeutic agents for treating a variety of diseases or conditions may be delivered using the nanotube-reinforced balloons described herein, including, but not limited to, therapeutic agents for treating restenosis. As used herein, "treatment" refers to the prevention of a disease or condition, the reduction or elimination of symptoms associated with a disease or condition, or the substantial or complete elimination of a disease or condition. Preferred subjects are vertebrate subjects, and more preferably mammalian subject, and still more preferably human subjects.

A wide variety of therapeutic agents may be delivered using the nanotube-reinforced balloons of the present invention. Some examples of therapeutic agents include pharmaceuticals, proteins, peptides, nucleotides, carbohydrates, polysaccharides, muccopolysaccharides, simple sugars, glycosaminoglycans, and steroids. For example, antithrombotics such as thrombin inhibitors, including hirudin, trigramin, prostacyclin and prostacyclin analogs, dextran, salicylates, PPACK, hirulog, heparin, heparinoids, argatroban, forskolin, vapiprost, D-phe-pro-arg-chloromethyl ketone (synthetic antithrombin), dipyridamole, Angiomax (Biogen Idec, Cambridge, Mass.), and platelet inhibitors such as 7E3 or other inhibitors of platelet receptor GPIIb/IIIa may be used. Thrombolytic agents may include streptokinase, urokinase, tissue plasminogen activator (TPA) and anisoylated plasminogen-streptokinase activator complex (APSAC). Antiproliferative agents may include antisense oligonucleotides, heparin, angiopeptin, angiotensin converting enzyme inhibitors such as captopril (e.g., Capoten and Capozide from Bristol-Myers Squibb, Co.), cilazapril or lisinopril (e.g., Prinivil and Prinzide from Merck & Co., Inc., Whitehouse Station, N.J.), and sumarin. Or, for example, anti-inflammatory agents, growth factors, smooth muscle cell migration and matrix degradation inhibitors, re-endothelialization agents, or any other drug or agent that eliminates, reduces, or otherwise inhibits the restenosis of a blood vessel may be used.

Some examples of therapeutic agents, at least some of which have been identified as candidates for inhibiting re-closure of a blood vessel (e.g., due to restenosis) include, but are not limited to: sirolimus, tacrolimus, everolimus, cyclosporine, natural and synthetic corticosteroids such as dexamethasone, M-prednisolone, leflunomide, mycophenolic acid, mizoribine, tranilast, biorest, estradiol, statins, paclitaxel (e.g., Taxol by Bristol-Myers Squibb Co., Stamford, Conn.), docetaxel (e.g., Taxotere from Aventis S.A., Frankfurt, Germany), Epo D, actinomycin (e.g., actinomycin D), azathioprine, fluorouracil, doxorubicin hydrochloride (e.g., Adriamycin from Pharmacia & Upjohn, Peapack, N.J.), geldanamycin, cilostazole, methotrexate, angiopeptin, vincristine, vinblastine, mitomycin (e.g., Mutamycin from Bristol-Myers Squibb Co.), QP-2, C-MYC antisense, ABT-578 (Abbott Laboratories), restenASE, choloro-deoxyadenosine, PCNA Ribozyme, batimastat, prolyl hydroxylase inhibitors, halofuginone, C-proteinase inhibitors, probucol, trapidil, liprostin, Resten-NG, Ap-17, abciximab, cladribine, clopidotrel, ridogrel, nitrates and calcium channel-blocking drugs such as nifedipine, colchicine, fibroblast growth factor (FGF) antagonists, fish oil (omega-3 fatty acid), histamine antagonists, lovastatin (an inhibitor of HMG-CoA reductace, a cholesterol lowering drug, brand name Mevacor from Merck & Co.), monoclonal antibodies (such as those specific for Platelet-Derived Growth Factor (PDGF) receptors), nitroprusside, phosphodiesterase inhibitors, prostaglandin inhibitors, suramin, serotonin blockers, thioprotease inhibitors, triazolopyramidine (a PDGF antagonist), nitric oxide, alpha-interferon, genetically engineered epithelial cells, dexamethasone, permirolast potassium, interleukins, and transformation growth factor b. Anti-inflammatory agents, both steroidal and non-steroidal and other agents which may modulate vessel tone, function, arteriosclerosis, and the healing response to vessel or organ injury post intervention may also be used. Such anti-inflammatory agents are also useful in connections such as inflammatory bowel disease, Crohn's disease, ulcerative colitis, and focal GI inflammatory diseases. Gene vector drugs, time-release drugs, and cancer-fighting drugs may also be delivered. Some examples of other appropriate therapeutic agents are set forth in U.S. Patent Publication No. 2004/0106987, entitled "Medical Devices for Delivery of Therapeutic Agents," the entire contents of which are incorporated herein by reference.

In one example, microspheres associated with stem cells, such as described in U.S. Pat. No. 7,338,657, the entire contents of which are incorporated by reference, are delivered either in solid form and delivered using a balloon such as illustrated in FIGS. 7A-8B or are dissolved in a liquid and delivered using a balloon such as illustrated in FIGS. 2B-2D or 6A-6B.

Radioactive therapeutic agents also may be used. For example, certain types of radiation therapy may reduce the risk of restenosis. Blood vessels exposed to a radioactive material such as cobalt-60, strontium-90, phosphorous-32, palladium-103, iridium-192, iodine-125, indium-114m, or cesium-131 have been found to experience less restenosis than blood vessels not exposed to such radioactive materials. Conventionally, blood vessels have been exposed to radioactive materials using specially fabricated radioactive guidewires, balloons, or stents. See U.S. Pat. No. 5,213,561, entitled "Methods and Devices for Preventing Restenosis After Angioplasty," and U.S. Pat. No. 7,311,655, entitled "Method for Manufacturing Radioactive Brachytherapy Source Material, Brachytherapy Source Material, and Encapsulated Radioactive Brachytherapy Source," the entire contents of both of which are incorporated herein by reference. In contrast, the nanotube-reinforced balloons of the present invention may be used to deliver a fluidic or particulate radioactive therapeutic agent within or beyond a blood vessel wall, allowing the blood vessel to be continuously exposed to an appropriate level of radiation without requiring the insertion of a radioactive stent or exposing the subject to a single large dose of radiation. Such radioactive therapeutic agents may be delivered to other types of body lumens in order to treat cancer.

The therapeutic agent may be in any form, including, but not limited to, fluids such as solutions, emulsions, particle dispersions, gels, and fluid particulates, and particulate solids such as pellets, granules, grains, beads, microcapsules, microspheres, nanospheres, microparticles, nanoparticles, and powders. Suitable particulate solids may have particle sizes ranging between, for example, 0.1 and 250 µm, e.g., 10-15 µm, or less than 10 µm. Particles larger than about 250

µm may also be delivered. The particles may have a density between about 0.1 and 25 g/cm$^3$, e.g., between about 0.9 and 1.5 g/cm$^3$, and may be injected with velocities between about 200 and 3000 m/s.

In some embodiments, the therapeutic agent is lipophilic, while in other embodiments, the therapeutic agent is hydrophobic, while in still other embodiments, the therapeutic agent is amphiphilic.

The therapeutic agent may be dispersed in any suitable pharmaceutically acceptable carrier. For example, paclitaxel may be dispersed in Cremophor EL (polyethoxylated castor oil, CAS number 61791-12-6, BASF Corp.), which is a synthetic, nonionic surfactant. Alternately, paclicaxel may be bound to a protein such as albumin, a formulation that may be commercially purchased under the trade name Abrexane (Abraxis Bioscience). Examples of other suitable pharmaceutically acceptable carriers include the biocompatible solvents dimethylsulfoxide, analogs/homologs of dimethylsulfoxide, ethanol, acetone, ethyl lactate, and the like. Aqueous solutions, such as water or saline, also may be used.

Examples of solid carriers for particulate therapeutic agents include biodegradable polymers such as gelatin, polylactic acid, polyglycolic acid, polycaprolactone, polydioxanon, starch, gelatin, and polyanhydrides or nondegradable polymers such as styrene or acrolein. Drug-containing liposomes also may be used. Tungsten, gold, platinum, and iridium carrier particles also may be used, e.g., having diameters between 0.2 and 3 µm.

Examples of suitable blood vessels for treatment using nanotube-reinforced balloons include renal, iliac, femoral, distal leg and carotid arteries as well as saphenous vein grafts, synthetic grafts and arterioveinous shunts used for hemodialysis. It is contemplated that the nanotube-reinforced balloon catheters described herein have applicability for use with any other type of body passageway, including, but not limited to, urethra, prostate, prostatic urethra, esophagus, fallopian tubes, rectum, intestines, bronchi, kidney ducts, wind pipe, pancreatic ducts, gall bladder ducts, brain parenchyma, and the like.

The term "contrast agent" refers to a biocompatible radiopaque material capable of being monitored during injection into a subject by, for example radiography. The contrast agent may be either water soluble or water insoluble and in some embodiments does not contain radioactivity above the native or endogenous amounts naturally occurring in the elements employed. Examples of water soluble contrast agents include metrizamide, iopamidol, iothalamate sodium, iodomide sodium, and megalumine. Examples of water insoluble contrast agents include tantalum, tantalum oxide, and barium sulfate, each of which is commercially available in the proper form for in vivo use including a particle size of about 10 µm or less. Other water insoluble contrast agents include gold, tungsten, and platinum powders.

Although various embodiments of the present invention are described above, it will be evident to one skilled in the art that various changes and modifications may be made without departing from the invention. It is intended in the appended claims to cover all such changes and modifications that fall within the true spirit and scope of the invention.

What is claimed:

1. A catheter for delivering a therapeutic agent into a wall of a body lumen, the wall having a thickness, the catheter comprising:
    an elongated shaft having proximal and distal ends and a lumen therebetween; and
    a balloon affixed to the elongated shaft near the distal end, the balloon consisting of a polymer with a plurality of nanotubes dispersed therein forming a flexible wall defining a plurality of pores apposition to the wall of the body lumen when the balloon is inflated, the pores being configured to reversibly transition between a closed state below a predefined pressure and an open state at or above the predefined pressure to inject the therapeutic agent into the wall of the body lumen.

2. The catheter of claim 1, further comprising:
    a pressurized reservoir of fluid in fluidic communication with the balloon via the lumen in the shaft; and
    an actuator for controllably inflating the balloon with the fluid at a pressure sufficient to bring the flexible wall of the balloon into contact with at least a portion of the wall of the body lumen but below the predefined pressure, and for controllably increasing the pressure of the fluid within the inflated balloon to at least the predefined pressure at a rate and with a force sufficient to deliver the therapeutic agent from the pores and through at least a portion of the thickness of the wall of the body lumen.

3. The catheter of claim 2, wherein the actuator controllably increases the pressure of the fluid within the inflated balloon to a selected pressure at a rate and with a force sufficient to deliver the therapeutic agent from the pores and through a entirety of at least one of a tunica intima, a tunica media, and a tunica adventitia of the body lumen.

4. The catheter of claim 2, wherein the fluid comprises the therapeutic agent and a pharmaceutically acceptable carrier, and wherein the actuator controllably increases the pressure of the fluid within the inflated balloon to at least the predefined pressure at a rate and with a force sufficient to jet the fluid through the pores and through at least a portion of the thickness of the wall of the body lumen.

5. The catheter of claim 1, wherein the nanotubes form a reinforcing web within the flexible wall.

6. The catheter of claim 1, wherein the nanotubes are substantially evenly dispersed in the polymer.

7. The catheter of claim 1, wherein the nanotubes are present in a concentration of less than 5% w/w in the polymer.

8. The catheter of claim 1, wherein the predefined pressure is based at least in part on a size of the pores, a thickness of the flexible wall, a composition of the polymer, and a concentration of nanotubes in the polymer.

9. The catheter of claim 1, wherein the therapeutic agent comprises an agent for creating an in-situ stent within the wall of the body lumen.

10. The catheter of claim 9, wherein the agent comprises at least one of an enzyme, a cross-linking agent, a small molecule, a protein, and an antibody selected to modify an elasticity of an intracellular matrix.

11. The catheter of claim 1, wherein the therapeutic agent is selected from the group consisting of: antithrombotics, thrombolytic agents, antiproliferative agents, anti-inflammatory agents, growth factors, smooth muscle cell migration and matrix degradation inhibitors, and re-endothelialization agents.

12. A method of delivering a therapeutic agent within a wall of a body lumen, the wall having a thickness, the method comprising:
    inserting into the body lumen at least a portion of a catheter comprising:
        an elongated shaft having proximal and distal ends and a lumen therebetween; and
        a balloon affixed to the elongated shaft near the distal end, the balloon consisting of a polymer with a plurality of nanotubes dispersed therein forming a flexible wall defining a plurality of pores positioned so as to be disposed in apposition to the wall of the body lumen when the balloon is inflated, the pores being configured to reversibly transition between a closed state below a predefined pressure and an open state at or above the predefined pressure to inject the therapeutic agent into the wall of the body lumen;

controllably inflating the balloon with a fluid at a pressure sufficient to bring the flexible wall of the balloon into contact with at least a portion of the wall of the body lumen but below the predefined pressure; and controllably increasing the pressure of the fluid within the inflated balloon to at least the predefined pressure at a rate and with a force sufficient to deliver the therapeutic agent from the pores and through at least a portion of the thickness of the wall of the body lumen.

13. The method of claim 12, wherein the nanotubes form a reinforcing web within the flexible wall.

14. The method of claim 12, wherein the nanotubes are substantially evenly dispersed in the polymer.

15. The method of claim 12, wherein the nanotubes are in a concentration of less than 5% w/w in the polymer.

16. The method of claim 12, comprising selecting a size of the pores, a thickness of the flexible wall, a composition of the polymer, and a concentration of nanotubes in the polymer to define the predefined pressure.

17. The method of claim 12, comprising increasing the pressure of the fluid within the inflated balloon to a selected pressure at a rate and with a force sufficient to deliver the therapeutic agent from the pores and through a entirety of at least one of a tunica intima, a tunica media, and a tunica adventitia of the body lumen.

18. The method of claim 12, wherein the fluid comprises the therapeutic agent and a pharmaceutically acceptable carrier, and comprising increasing the pressure of the fluid within the inflated balloon to at least the predefined pressure at a rate and with a force sufficient to jet the fluid through the pores and through at least a portion of the thickness of the wall of the body lumen.

19. The method of claim 12, wherein the therapeutic agent comprises an agent for creating an in-situ stent within the wall of the body lumen.

20. The method of claim 19, wherein the agent comprises at least one of an enzyme, a cross-linking agent, a small molecule, a protein, and an antibody selected to modify an elasticity of an intracellular matrix.

21. The method of claim 12, wherein the therapeutic agent is selected from the group consisting of: antithrombotics, thrombolytic agents, antiproliferative agents, anti-inflammatory agents, growth factors, smooth muscle cell migration and matrix degradation inhibitors, and re-endothelialization agents.

* * * * *